US008691188B2

(12) United States Patent
Marchese et al.

(10) Patent No.: US 8,691,188 B2
(45) Date of Patent: Apr. 8, 2014

(54) METHODS OF UTILIZING THE ARRESTIN-2/STAM-1 COMPLEX AS A THERAPEUTIC TARGET

(75) Inventors: Adriano Marchese, Westchester, IL (US); Rohit Malik, Forest Park, IL (US)

(73) Assignee: Loyola University Chicago, Maywood, IL (US)

( * ) Notice: Subject to any disclaimer, the term of this patent is extended or adjusted under 35 U.S.C. 154(b) by 0 days.

(21) Appl. No.: 13/115,666

(22) Filed: May 25, 2011

(65) Prior Publication Data
US 2012/0059044 A1 Mar. 8, 2012

Related U.S. Application Data

(60) Provisional application No. 61/348,724, filed on May 26, 2010.

(51) Int. Cl.
| A61K 49/00 | (2006.01) |
| C12Q 1/68 | (2006.01) |
| C12P 19/34 | (2006.01) |
| C12P 21/06 | (2006.01) |
| C07H 21/04 | (2006.01) |

(52) U.S. Cl.
USPC .......................................................... 424/9.2

(58) Field of Classification Search
USPC ............ 424/9.1, 9.2; 435/6, 91.1, 91.31, 455, 435/69.1; 514/1, 2, 44; 536/23.1, 24.5
See application file for complete search history.

(56) References Cited

PUBLICATIONS

Abella, J.V., Preschard, P., Naujokas, M.A., Lin, T., Saucier, C., Urbe, S., and Park, M.; (2005); Met/Hepatocyte growth factor receptor ubiquitination suppresses transformation and is required for Hrs phosphorylation, Mol. Cell Biol. 25, 9632-9645.
Asao, H., Sasaki, Y., Arita, T., Tanaka, N., Endo, K., Kasai, H., Takeshita, T., Endo, Y., Fujita, T., and Sugamura, K.; (1997); Hrs is associated with STAM, a signal-transducing adaptor molecule; its suppressive effect on cytokine-induced cell growth; J. Biol. Chem. 272, 32785-32791.
Bache, K.G., Brech, A., Mehlum, A., and Stenmark, H. (2003a); Hrs regulates multivesicular body formation via ESCRT recruitment to endosomes; J. Cell Biol. 162, 435-442.
Bache, K.G., Raiborg, C., Mehlum, A., and Stenmark, H. (2003b); STAM and Hrs are subunits of a multivalent ubiquitin-binding complex on early endosomes; J. Biol. Chem. 278,12513-12521.
Bhandari, D., Robia, SL.L., and Marchese, A. (2009); The E3 ubiquitin ligase atrophin interacting protein 4 binds directly to the chemokine receptor CXCR4 via a novel WW domain-mediated interaction; Mol. Biol. Cell 20, 1324-1339.
Bhandari, D., Trejo, J., Benovic, J.L., and Marchese, A. (2007) Arrestin-2 interacts with the ubiquitin-protein isopeptide ligase atrophin-interacting protein 4 and mediates endosomal sorting of the chemokine receptor CXCR4; J. Biol. Chem. 282, 36971-36979.
Bowers, K, Piper, S.C., Edeling, M.A., Gray, S.R., Owen, D.J., Lehner, P.J. and Luzio, J.P. (2006); Degradation of endocytosed epidermal growth factor and virally ubiquitinated major histocompatibility complex class I is independent of mammalian ESCRTII; J. Biol.Chem., 281, 5094-5105.
Busillo, J.M., Armando, S., Sengupta, R., Meucci, O., Bouvier, M. and Benovic, J.L. )2010); Site-specific phosphorylation of CXCR4 is dynamically regulated by multiple kinases and results in differential modulation of CXCR4 signaling; J. Biol. Chem., 285, 7805-7817.
Endo, K., Takeshita, T., Kasai, H., Sasaki, Y., Tanaka, N., Asao, H., Kikuchi, K., Yamada, M., Chenb, M., O'Shea, J.J., and Sugamura, K. (2000); STAM2, a new member of the STAM family, binding to the Janus kinases; Febs Lett., 477, 55-61.
Hasdemir, B., Bunnett, N. W., and Cottrell, G.S. (2007); Hepatocyte growth factor-regulated tyrosine kinase substrate (Hrs) mediates post-endocytic trafficking of protease-activated receptor 2 and calcintonin receptor-like receptor.
Hasdemir, B., Murphy, J.E., Cottrell, G.S., and Bunnett, N. W. (2009); Endosomal deubiquitinating enzymes control ubiquitination and down-regulation of protease-activated receptor 2; J. Biol. Chem., 284, 28453-28466.
Herrador, A., Herranz, S., Lara, D., and Vincent, O. (2010); Recruitment of the Escrt machinery to a putative seven-transmembrane-domain receptor is mediated by an arrestin-related protein; Mol. Cell Biol., 30, 897-907.
Hirano, S., Kawasaki, M., Ura, H., Kato, R., Raiborg, C., Stenmark, H., and Wakatsuki, S. (2006); Double-sided ubiquitin binding of Hrs-UIM in endosomal protein sorting; Nat. Struct. Mol. Biol; 13, 272-277.
Hoeller, D., Crosetto, N., Blagoev, B., Raiborg, C., Tikkanen, R., Wagner, S., Kowanetz, K., Breitling, R., Mann, M., Stenbmark, H., and Dikic, I. (2006); Regulation of ubiquitin-binding proteins by monoubiquitination; Nat. Cell Biol.; 8, 163-169.
Kanazawa, C., Morita, E., Yamada, M., Ishii, N, Miura, S., Asao, H., Yoshimori, T., and Sugamura, K. (2003); Effects of deficiencis of STAMs and Hrs, mammalian class E vps proteins, on receptor downregulation; Biochem. Biophys. Res. Commun.; 309, 848-856.
Kern, R.C., Kang, D.S., and Benovic, J.L. (2009); Arresting/clathrin interaction is regulated by key N- and C-terminal regions in arresting; Biochemistry 48, 7190-7200.
Kong, C., Su, X, Chen, P.I., and Stahl, P.D. (2007); Rin1 interacts with signal-transducing adaptor molecule (STAM) and mediates epidermal growth factor receptor trafficking and degradation; J. Biol. Chem., 282, 15294-15301.
Kovacs, J.J., Hara, M.R., Davenport, C.L., Kim, J., and Lefkowitz, R.J. (2009); Arrestin development; emerging roles for beta-arrestins in developmental signaling pathways; Dev. Cell 17; 443-458.

(Continued)

Primary Examiner — Jane Zara
(74) Attorney, Agent, or Firm — Hartman Global IP Law; Gary M. Hartman; Domenica N. S. Hartman

(57) ABSTRACT

Methods of utilizing the arrestin-2/sTAM-1 complex as a therapeutic target. The methods include treating cells of a living organism to mediate an interaction between arrestin-2 and STAM-1 adapter protein molecules, wherein the interaction is characterized by the arrestin-2 adapter protein molecule directly binding to the STAM-2 adapter protein molecule. Pharmacological agents can be identified for therapeutic uses by determining whether the pharmacological agent disrupts the interaction between the arrestin-2 and STAM-1 adapter protein molecules.

19 Claims, 16 Drawing Sheets

(56) References Cited

PUBLICATIONS

Loshi, O., Poussu, A., Merilainen, J., Kellokumpu, S., Wasenius, V.M., and Lehto, V.P. (1998); East, an epidermal growth factor receptor- and Eps15-associated protein with Src homology 3 and tyrosine-based activation motif domains; J. Biol. Chem; 273, 21408-21415.

Ma, Y.M., Boucrot, E., Villen, J., Affar El, B., Gygi, S.P., Gottlinger, H.G., and Kirchhausen, T., (2007); Targeting of AMSH to endosomes is required for epidermal growth factor receptor degradation; J. Biol. Chem., 282, 9805-9812.

Marchese, A. (2009) Ubiquitination of chemokine receptors; Methods Enzymol; 460, 413-422.

Marchese, A., and Benovic, J.L. (2001); Agonist-promoted ubiquitination of the G protein-coupled receptor CXCR4 mediates lysosomal sorting; J. Biol. Chem.; 276, 45509-45512.

Marchese, A., Raiborg, C., Santini, F., Keen, J.H., Stenmark, H., and Benovic, J.L. (2003); The E3 ubiquitin ligase AIP4 mediates ubiquitination and sorting of the G protein-coupled receptor CXCR4; Dev. Cell 5, 709-722;.

Mccullough, J., Clague, M.J., and Urbe, S. (2004); AMSH is an endosome-associated ubiquitin isopeptidase; J. Cell Biol.; 166, 487-492.

Mccullough, J., Row, P.E., Lorenzo, O., Doherty, M., Beynon, R., Clague, M.J., and Urbe, S. (2006); Activation of the endosome-associated ubiquitin isopeptidase AMSH by STAM, a component of the multivesicular body-sorting machinery; Curr. Biol. 16, 160-165.

Moore, C.A., Milano, S.K., and Benovic, J.L. (2007); Regulation of receptor trafficking by GRKs and arrestins; Ann. Rev. Phy. 69, 451-482.

Pandey, A., Fernandez, M.M. Steen, H., Blagoev, B., Nielsen, M.M., Roche, S., Mann, M. and Lodish, H.F. (2000); Identification of a novel immunoreceptor tyrosine-based activation motif-containing molecule, STAM2, by mass spectrometry and its involvement in growth factor and cytokine receptor signaling pathways; J. Biol. Chem., 275, 38633-38639.

Prag, G., Watson, H., Kim, Y.C., Beach, B.M., Ghirlando, R., Hummer, G., Bonifacino, J.S., and Hurley, J.H. (2007); the Vps27/Hse1 complex is a GAT domain-based scaffold for ubiquitin-dependent sorting; Dev. Cell 12, 973-986.

Raiborg, C., and Stenmark, H. (2009); The ESCRT machinery in endosomal sorting of ubiquitylated membrane proteins; Nature 458, 445-452.

Ren, X., Kloer, D.P., Kim, Y.,C., Ghirlando, R., Saidi , L.F., Hummer, G., and Hurley, J.H. (2009); Hybrid structural model of the complete human ESCRT-0 complex; Structure 17, 406-416.

Rismanchi, N., Puertollano, R., and Blackstone, C. (2009); STAM adaptor proteins interact with COPII complexes and function in ER-to-Golgi trafficking; Traffic 10, 201-217.

Row, P.E., Prior, I.A., Mccullough, J., Clague, M.J., and Urbe, S. (2006); The ubiquitin isopeptidase UBPY regulates endosomal ubiquitin dynamics and is essential for receptor down-regulation; J. Biol. Chem., 281, 12618-12624.

Shenoy, S.K., McDonald, P.H., Kohout, T.A., and Lefkowitz, R.J. (2001); Regulation of receptor fate by ubiquitination of activated beta 2-adrenergic receptor and beta-arrestin; Science 294, 1307-1313.

Shenoy, S.K., Modi, A.S., Shukla, A.K., Xiao, K., Berthouze, M., Ahn, S., Wilkinson, K.D., Miller, W.E., and Lefkowitz, R.J. (2009); Beta-arrestin-dependent signaling and trafficking of 7-transmembrane receptors is reciprocally regulated by the deubiquitinase USP33 and the E3 ligase; Mdm2. Proc. Nat. Acad. Sci., USA 106, 6650-6655.

Shields, S.B., Oestreich, A.J., Winistorfer, S., Nguyen, D., Payne, J.A., Katzmann, D.J., and Piper, R. (2009); ESCRT ubiquitin-binding domains function cooperatively during MVB cargo sorting; J. Cell Biol., 185, 213-224.

Sierra, M.I., Wright, M.H., and Nash, P. (2010); AMSH interacts with ESCRT-0 to regulate the stability and trafficking of CXCR4; J. Biol. Chem., jbc.M109.061309 First Published on Feb. 16, 2010, doi: 10.1074/jbc. M109.061309.

Takata, H., Kato, M., Denda, K., and Kitamura, N. (2000); A hrs binding protein having a SRC homology 3 domain is involved in intracellular degradation of growth factors and their receptors; Genes Cells 5, 57-69.

Takeshita, T., Arita, T., Asao, H., Tanaka, N., Higuchi, M., Kuroda, H., Kaneko, K., Munakata, H., Endo, K., Fujita, T., and Sugamura, K. (1996); Cloning of a novel signal-transducing adaptor molecule containing an SH3 domain and ITAM; Biochem. Biophys. Res. Commun., 225, 1035-1039.

Takeshita, T., Arita, T., Higuchi, M., Asao, H. Endo, K., Kuroda, H., Tanaka, N., Murata,K., Ishii, N., and Sugamura, K. (1997); STAM, signal transducing adaptor molecule, is associated with Janus kinases and involved in signaling for cell growth and c-myc induction; Immunity 6, 449-457.

Vishnivetskiy, S.A., Schubert, C., Climaco, G.C., Gurevich, Y.V., Velez, M.G., and Gurevich, V.V. (2000); An additional phosphate-binding element in arrestin molecule; Implications for the mechanism of arrestin activation; J. Biol. Chem. 275, 41049-41057.

Williams, R.L., and Urbe, S. (2007); The emerging shape of the ESCRT machinery; Nat. Rev. Mol. Cell biol. 8, 355-368.

Yamada, M., Ishii, N., Asao, H., Murata, K., Kanazawa, C., Sasaki, H., and Sugamura, K. (2002); Signal-transducing adaptor molecules STAM1 and STAM2 are required for T-cell development and survival; Mol.CellBiol. 22, 8648-8658.

Figure 4
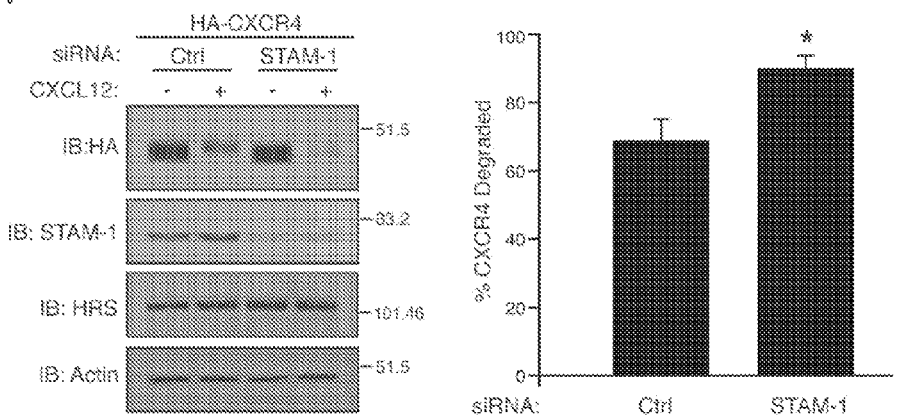
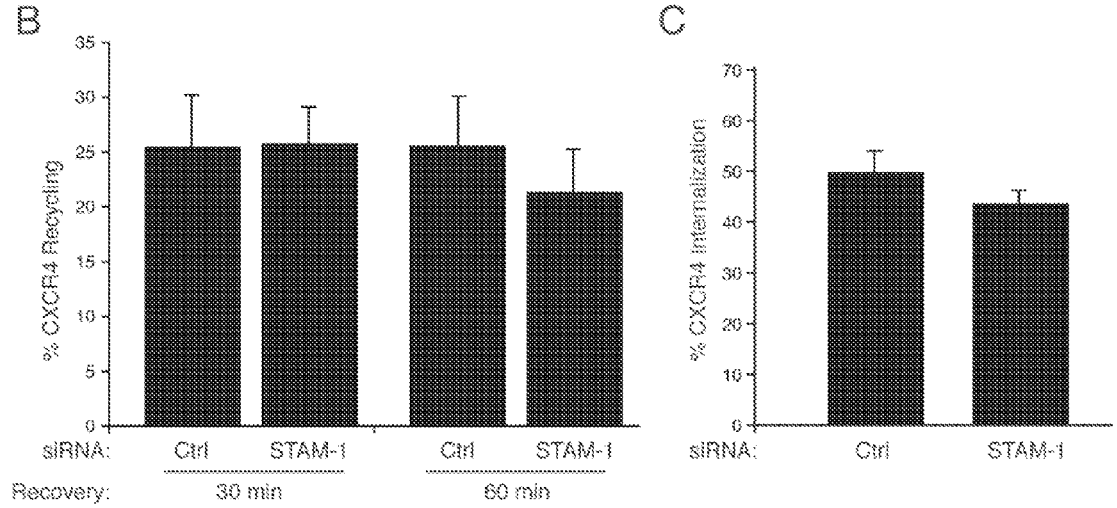
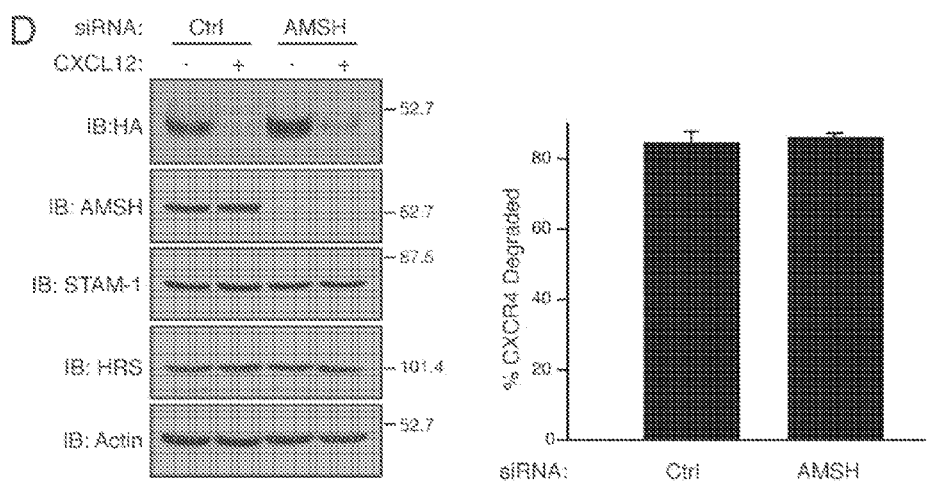

A
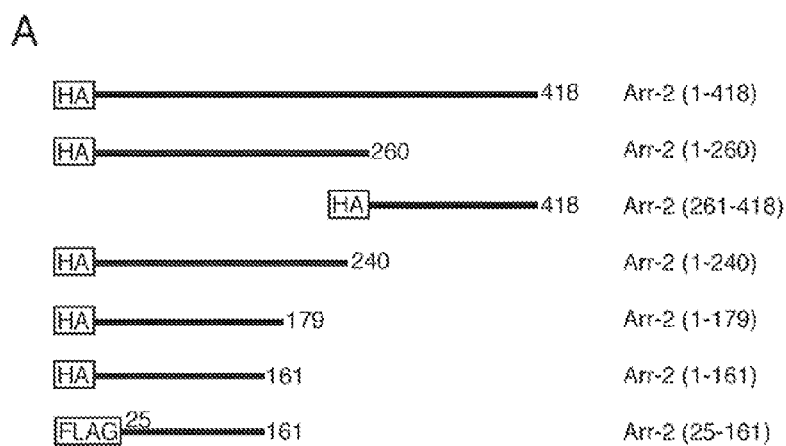
B
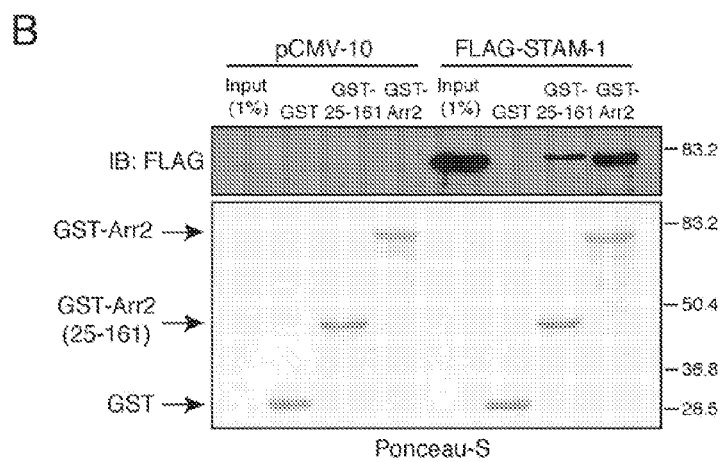
C
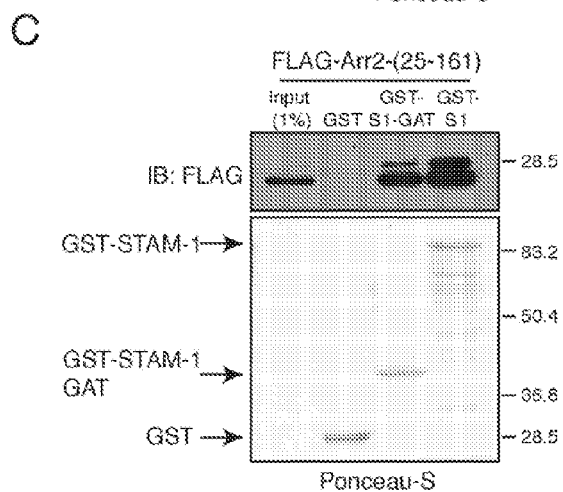
Figure 7

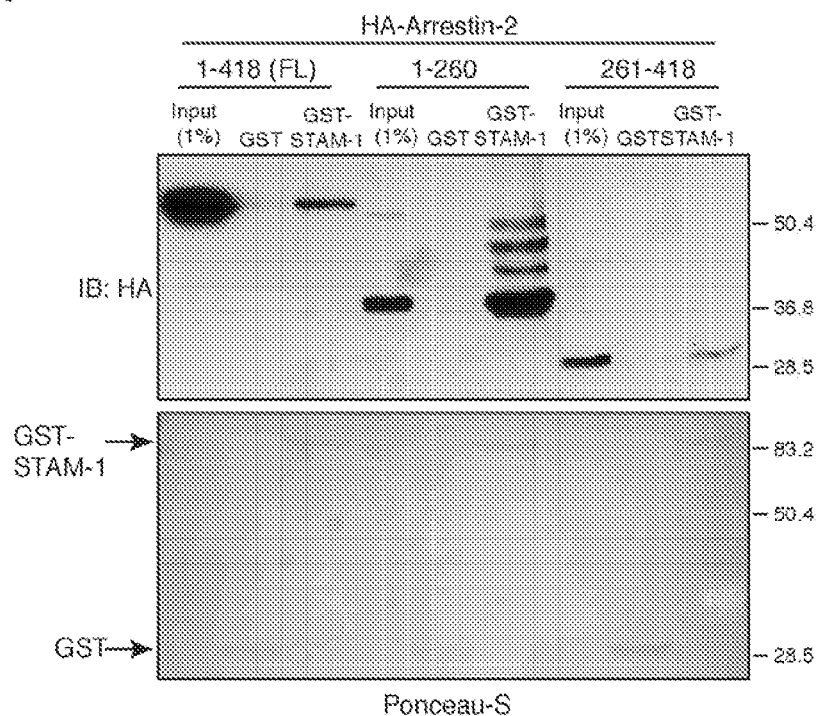
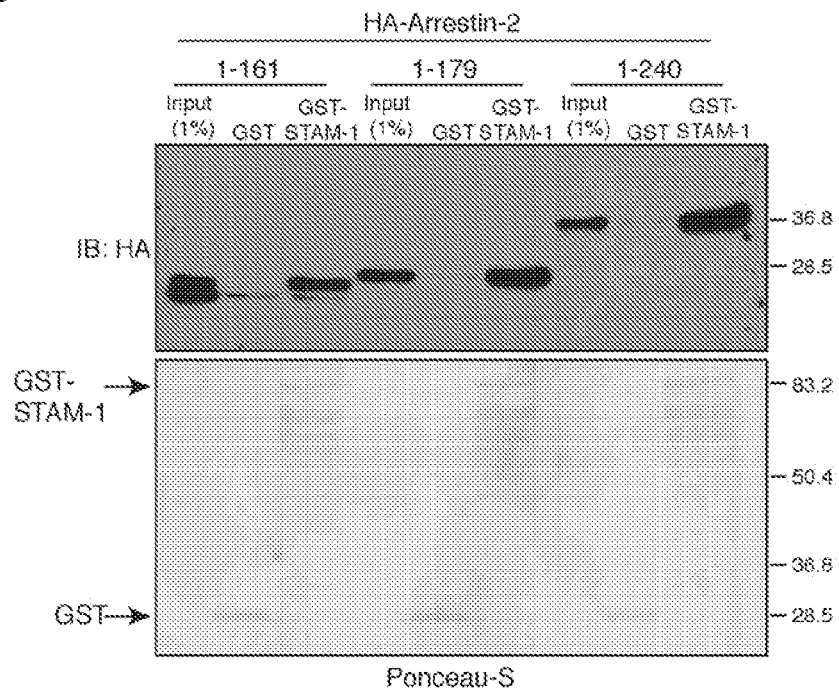
Figure 12

List of primers used to make constructs described in this study

| | Construct Name | Primers (5'→3') |
|---|---|---|
| 1. | FLAG-STAM-1 (1-195) | Forward: GGAGGTCTATATAAGCAGAGC<br>Reverse: ATATTCTAGATTAGGAAAGGGTGGTTGACTGCTG |
| 2. | FLAG-STAM-1 (1-269) | Forward: GGAGGTCTATATAAGCAGAGC<br>Reverse: ATATTCTAGATTAAGTGAGATCTGCAGTCACAAA |
| 3. | FLAG-STAM-1 (1-390) | Forward: GGAGGTCTATATAAGCAGAGC<br>Reverse: ATATTCTAGATTACTGATTCTGTAACTTTGCATA |
| 4. | FLAG-STAM1 (391-540) | Forward: ATATAAGCTTCCATATATATGCAG<br>Reverse: GGGCCAGGAGAGGCACTG |
| 5. | FLAG-STAM-1 (144-540/ΔVHS) | Forward: ATATAAGCTTGCTATTGGCTCTCAGGCT<br>Reverse: GGGCCAGGAGAGGCACTG |
| 6. | FLAG-STAM-1 (337-540) | Forward: ATATAAGCTTCACCAGATGGGACCTCTC<br>Reverse: GGGCCAGGAGAGGCACTG |
| 7. | FLAG-STAM-1 (212-540) | Forward: ATATAAGCTTGGCCGAAAAGTTCGTGC<br>Reverse: GGGCCAGGAGAGGCACTG |
| 8. | FLAG-STAM-1 (270-540) | Forward: ATATAAGCTTGCTGAACCAGAAATGATT<br>Reverse: GGGCCAGGAGAGGCACTG |
| 9. | FLAG-STAM-1- Delta GAT (Δ343-377) | Forward 1: TGTCACCAGATGGGACCTCTGGATCGGATGTATTCCATGTATGC<br>Reverse 1: GAGAGGTCCCATCTGGTGACA<br>Forward 2: GGAGGTCTATATAAGCAGAGC<br>Reverse 2: GGGCCAGGAGAGGCACTG |
| 10. | GST-STAM-1-Delta GAT (Δ343-377) | Forward: ATATGAATTCGCTCTCTTTTGCCACCAATCCC<br>Reverse: ATATCTCGAGTCTATAGCAGAGCCTTCTG |
| 11. | GST-STAM-1-GAT (296-380) | Forward: ATATGAATTC TGGAGCCGGAACCAGCC<br>Reverse: ATATCTCGAGTCACATCGGATCTTCGTTCATTAAC |
| 12. | FLAG-STAM-1-GAT (296-380) | Forward: ATAT AAG CTT GAG CCG GAA CCA GCC<br>Reverse: ATATTCTAGACTACATCGGATCTTCGTTCATTAAC |
| 13. | YFP-STAM-1 | Forward: ATATAAGCTTTGCCTCTCTTTTGCCACCAATCCCTTC<br>Reverse: ATATGGTACCTACCTACATCGGATCTTCGTTCATTAAC |
| 14. | FLAG-Arr-2-(25-161) | Forward: ATATAAGCTTCGGGACTTTGTGGACCAC<br>Reverse: CAAACAACAGATGGCTGCAAC |
| 15. | GST-Arr-2-(25-161) | Forward: ATATCCCGGCGGGACTACCGCTTGTGGACCAC<br>Reverse: ATATCTCGAGCTACCGCTTGTGGATCTTCTCTCCA |

Figure 14

METHODS OF UTILIZING THE ARRESTIN-2/STAM-1 COMPLEX AS A THERAPEUTIC TARGET

CROSS REFERENCE TO RELATED APPLICATIONS

This application claims the benefit of U.S. Provisional Application No. 61/348,724, filed May 26, 2010, the contents of which are incorporated herein by reference.

STATEMENT REGARDING FEDERALLY SPONSORED RESEARCH

This invention was made with government support by National Institutes of Health (NIH) grant GM075159.

BACKGROUND OF THE INVENTION

The present invention generally relates to the use of the arrestin-2/STAM-1 complex as a therapeutic target, for example, to identify and develop pharmacological agents capable of treating medical diseases, such as the treatment of metastasis in cancer patients and myocardial infarction.

Chemokines are a family of small cytokines, or proteins, that are secreted by cells of certain organisms, and in particular the cells of all vertebrates. Chemokines interact with G protein-linked transmembrane receptors, or chemokine receptors, found on the surfaces of their target cells. Of interest to the present invention are the CXC family of chemokines (α-chemokines), and in particular the CXC chemokine receptors (CXCR) to which CXC chemokines bind.

The CXC chemokine receptor 4 (CXCR4), a G protein-coupled receptor (GPCR), upon activation by its cognate ligand stromal-cell derived factor-1α (SDF-1α/CXCL12), is known to be rapidly internalized and targeted into the degradative pathway by a ubiquitin-dependent mechanism. See Marchese, A., and Benovic, J. L., Agonist-promoted ubiquitination of the G protein-coupled receptor CXCR4 mediates lysosomal sorting, J. Biol. Chem. 276, 45509-45512 (2001); Shenoy, S. K., McDonald, P. H., Kohout, T. A., and Lefkowitz, R J., Regulation of receptor fate by ubiquitination of activated beta 2-adrenergic receptor and beta-arrestin, Science 294, 1307-1313 (2001); and Marchese, A., Raiborg, C., Santini, F., Keen, J. H., Stenmark, H., and Benovic, J. L., The E3 ubiquitin ligase AIP4 mediates ubiquitination and sorting of the G protein-coupled receptor CXCR4, Dev. Cell 5, 709-722 (2003). Activation by CXCL12 induces rapid and transient phosphorylation of serine residues 324 and 325 within the carboxyl-terminal tail (C-tail) of CXCR4, thereby promoting binding to the E3 ubiquitin ligase atrophin-I interacting protein 4 (AIP4) via a novel WW-domain mediated interaction culminating in ubiquitination of vicinal lysine residues (Marchese et al. (2003); Bhandari, D., Robia, S. L., and Marchese, A., The E3 ubiquitin ligase atrophin interacting protein 4 binds directly to the chemokine receptor CXCR4 via a novel WW domain-mediated interaction, Mol. Biol. Cell. 20, 1324-1339 (2009)). This is followed by internalization of CXCR4 onto early endosomes where the ubiquitin moiety serves as a sorting signal to direct the receptor to lysosomes for proteolysis (Marchese and Benovic (2001); Marchese et al. (2003)).

In general, the ubiquitin moiety on ubiquitinated receptors interacts with ubiquitin binding domains (UBD) found in several proteins of the endosomal sorting complex required for transport (ESCRT) machinery (Raiborg, C., and Stenmark, H., The ESCRT machinery in endosomal sorting of ubiquitylated membrane proteins, Nature 458, 445-452 (2009); Shields, S. B., Oestreich, A. J., Winistorfer, S., Nguyen, D., Payne, J. A., Katzmann, D. J., and Piper, R., ESCRT ubiquitin-binding domains function cooperatively during MVB cargo sorting, J. Cell Biol. 185, 213-224 (2009)). The ESCRT machinery is made up of four distinct protein complexes (ESCRT 0-III) that act in a sequential and coordinated manner to target ubiquitinated receptors into multivesicular bodies, which then fuse with lysosomes where degradation occurs. Recruitment into this pathway takes place by the initial recognition of the ubiquitinated receptor by ESCRT-0, which then subsequently recruits ESCRT-I to the endosomal membrane, followed by recruitment of ESCRT II and III, culminating in proper execution of the sorting process (Williams, R. L., and Urbe, S., The emerging shape of the ESCRT machinery, Nat. Rev. Mol. Cell Biol. 8, 355-368 (2007); Raiborg and Stenmark (2009)). Hepatocyte growth factor-regulated tyrosine kinase substrate (HRS) is understood to be a critical element of ESCRT-0 and has been shown to mediate down regulation of several cell surface signaling receptors (Bache, K. G., Brech, A., Mehlum, A., and Stenmark, H., Hrs regulates multivesicular body formation via ESCRT recruitment to endosames, J. Cell Biol. 162, 435-442 (2003); Kanazawa, C., Morita, E., Yamada, M., Ishii, N., Miura, S., Asao, H., Yoshimori, T., and Sugamura, K., Effects of deficiencies of STAMs and Hrs, mammalian class E Vps proteins, on receptor downregulation, Biochem. Biophys. Res. Commun. 309, 848-856 (2003); Abella, J. V., Peschard, P., Naujokas, M. A., Lin, T., Saucier, C., Urbe, S., and Park, M., Met/Hepatocyte growth factor receptor ubiquitination suppresses transformation and is required for Hrs phosphorylation, Mol. Cell Biol. 25, 9632-9645 (2005); Hasdemir, B., Bunnett, N. W., and Cottrell, G. S., Hepatocyte growth factor-regulated tyrosine kinase substrate (HRS) mediates post-endocytic trafficking of protease-activated receptor 2 and calcitonin receptor-like receptor, J. Biol. Chem. 282, 29646-29657 (2007)). One such cell surface signaling receptor is CXCR4 (Marchese et al. (2003)). The ubiquitin moiety on CXCR4 is thought to interact with the ubiquitin interacting motif (UIM) found in HRS, thereby targeting CXCR4 into the degradative pathway.

Together with HRS, signal-transducing adaptor molecule (STAM) forms ESCRT-O, STAM was originally identified as an adaptor protein involved in cytokine signaling (Takeshita, T., Arita, T., Asao, H., Tanaka, N., Higuchi, M., Kuroda, H., Kanecko, K., Munakata, H., Endo, Y., Fujita, T., and Sugamura, K.; Cloning of a novel signal-transducing adaptor molecule containing an SH3 domain and ITAM, Biochem, Biophys, Res. Commun. 225, 1035-1039 (1996); Takeshita, T., Arita, T., Higuchi, M., Asao, H., Endo, K., Kuroda, H., Tanaka, N., Murata, K., Ishii, N., and Sugamura, K.; STAM, signal transducing adaptor molecule, is associated with Janus kinases and involved in signaling for cell growth and c-myc induction, Immunity 6, 449-457; (1997). Two STAM isoforms exist, STAM-1 and STAM-2, which share 53% amino acid identity and may be redundant in their function (Lohi, O., Poussu, A., Merilainen, J., Kellokumpu, S., Wasenius, V. M., and Lehto, V. P., EAST, an ipidermal growth factor receptor- and Eps 15-associated protein with Src homology 3 and tyrosine-based activation motif domains, J. Biol. Chem., 273, 21408-21415 (1998); Endo, K., Takeshita, T., Kasai, H., Sasaki, Y., Tanaka, N., Asao, H., Kikuchi, K., Yamada, M., Chenb, M., O'Shea, J. J., and Sugamura, K., STAM2, a new member of the STAM family, bindign to the Janus kinases, FEBS Lett, 477, 55-61 (2000); Pandey, A., Fernandez, M. M., Steen, H., Blagoev, B., Nielsen, M. M., Roche, S., Mann, M., and Lodish, H. F., Identification of a novel immunoreceptor tyrosine-based activation motif-containing molecule, STAM2, by mass spectrometry and its involvement in growth factor and cytokine receptor signaling pathways, J. Biol. Chem., 275, 38633-38639 (2000); Yamada, M., Ishii, N., Asao, H., Murata, K., Kanazawa, C., Sasaki, H., and Sugamura, K., Signal-transducing adaptor molecules STAM1 and STAM2 are required for T-cell development and survival, Mol. Cell Biol., 22, 8648-8658 (2002). Similar to HRS, STAM also binds to ubiquitin and may act in concert with HRS to recruit ubiquitinated receptors for lysosomal sorting (Asao, H., Sasaki, Y., Arita, T., Tanaka, N., Endo, K., Kasai, H., Takeshita, T., Endo, Y., Fujita, T., and Sugamura, K., Hrs is associated with STAM, a signal-transducing adaptor molecule, Its suppressive effect on cytokine-induced cell growth, J. Biol. Chem., 272, 32785-32791 (1997); Takata, H., Katao, M., Denda, K., and Kitamura, N., A hrs binding protein having a Src homology 3 domain is involved in intracellular degradation of growth factors and their receptors, Genes Cells 5, 57-69 (2000); Bache, K. G., Raiborg, C., Mehlum, A., and Stenmark, H., STAM and Hrs are subunits of a multivalent ubiquitin-binding complex on early endosomes, J. Biol. Chem., 278, 12513-12521 (2003b); Kanazawa et al., (2003). STAMs may also modulate endosomal sorting by virtue of their ability to interact with endosomal associated deubiquitinating enzymes AMSH (associated molecule with the SH3 domain of STAM) and UBPY, which may modulate the ubiquitination status of both receptors and/or the sorting machinery (McCullough, J., Clague, M. J., and Urbe, S., AMSH is an endosome-associated ubiquitin isopeptidase, J. Cell Biol., 166, 487-492 (2004); Bowers, K., Piper, S. C., Edeling, M. A., Gray, S. R., Owen, D. J., Lehner, P. J., and Luzio, J. P., Degradation of endocytosed epidermal growth factor and virally ubiquitinated major histocompatibility complex class I is independent of mammalian ESCRTII, J. Biol. Chem., 281, 5094-5105 (2006); McCullough, J., Row, P.e., Lorenzo, O., Doherty, M., Beynon, R., Clague, M. J., and Urbe, S., Activation of the endosome-associated ubiquitin isopeptidase AMSH by STAM, a component of the multivesicular body-sorting machinery, Curr. Biol., 16, 160-165 (2006); Row, P. E., Prior, L. A., McCullough, J., Clague, M. J., and Urbe, S., The ubiquitin isopeptidase UBPY regulates endosomal ubiquitin dynamics and is essential for receptor down-regulation, J. Biol. Chem., 281, 12618-12624 (2006); Kong, C., Su, X., Chen, P. I., and Stahl, P. D., Rin1 interacts with signal-transducing adaptor molecule (STAM) and mediates epidermal growth factor receptor trafficking and degradation, J. Biol. Chem., 282, 15294-15301 (2007); Ma, Y. M., Boucrot, E., Villen, J., Affar el, B., Gygi, S. P., Gottlinger, H. G., and Kirchhausen, T., Targeting of AMSH to endosomes is required for epidermal growth factor receptor degradation, J. Biol. Chem., 282, 9805-9812 (2007). Recently, STAMs have been implicated in endoplasmic reticulum to Golgi trafficking, possibly via their interaction with coat protein II proteins (Rismanchi, N., Puertollano, R., and Blackstone, C., STAM adaptor proteins interact with COPII complexes and function in ER-to-Golgi trafficking, Traffic 10, 201-217 (2009). However, their role in GPCR trafficking and signaling is believed to be relatively unknown.

It has been recently shown that arrestin-2 mediates endosomal sorting of CXCR4 (Bhandari, D., Trejo, J., Benovic, J. L., and Marchese, A., Arrestin-2 interacts with the ubiquitin-protein isopeptide ligase atrophin-interacting protein 4 and mediates endosomal sorting of the chemokine receptor CXCR4, J. Biol. Chem., 282, 36971-36979 (2007). Non-visual arrestins, arrestin-2 and arrestin-3 (also known as β-arrestin1 and β-arrestin2, respectively), are generally known for their ability to regulate GPCR desensitization, internalization and signaling (Moore, C. A., Milano, S. K., and Benovic, J. L., Regulation of receptor trafficking by GRKs and arrestins, Ann. Rev. Phy., 69, 451-482 (2007), although their role in endosomal sorting remains relatively unexplored. Arrestin-2 interacts with and co-localizes with AIP4 on early endosomes, where it targets CXCR4 for lysosomal sorting (Bhandari et al., 2007). In addition to mediating ubiquitination of CXCR4 at the plasma membrane, AIP4 also interacts with and mediates ubiquitination of HRS, likely on endosomes. However, the function of the ubiquitin moiety remains unknown (Marchese et al., 2003). How arrestin-2 may integrate with AIP4 and HRS to carry out CXCR4 sorting into the degradative pathway remains poorly understood.

It is believed that others have used pharmacological agents that directly target CXCR4 to antagonize agonist (CXCL12) evoked CXCR4 signaling mediated events. A major disadvantage of this approach is that directly targeting CXCR4 is not specific, as it would modulate all intracellular signaling cascades activated by CXCR4. A major caveat with this approach is that it has the potential of producing unintended consequences, such as deleterious side-effects.

BRIEF DESCRIPTION OF THE INVENTION

The present invention provides methods of utilizing the arrestin-2/STAM-1 complex as a therapeutic target.

According to a first aspect of the invention, a method is provided that includes treating cells of a living organism to mediate an interaction between an arrestin-2 adapter protein molecule and a STAM-1 adapter protein molecule, wherein the interaction is characterized by the arrestin-2 adapter protein molecule directly binding to the STAM-1 adapter protein molecule. The treatment preferably involves subjecting a cell of the living organism to a pharmacological agent, and then determining whether the pharmacological agent modulates, for example, disrupts or enhances, the interaction between the arrestin-2 adapter protein molecule and the STAM-1 adapter protein molecule.

According to a second aspect of the invention, a method is provided that involves identifying a pharmacological agent to treat metastasis of a cancer in living organisms. The method includes treating cells of a living organism with the pharmacological agent, and then determining whether the pharmacological agent disrupts an interaction (binding) between an arrestin-2 adapter protein molecule and a STAM-1 adapter protein molecule of cells of the living organism. If the pharmacological agent disrupts the interaction, the method may further entail treating a second living organism with the pharmacological agent to treat metastasis of a cancer in the second living organism, for example, by decreasing CXCR4 levels and/or inhibiting CXCL12-evoked cell migration in the second living organism.

A technical effect of the invention is the ability to interact arrestin-2 with the ESCRT machinery to modulate endosomal sorting of CXCR4. In particular, an interaction between the adaptor proteins arrestin-2 and STAM-1 has been identified that enables the arrestin-2/STAM-1 complex to be used as a therapeutic target to modulate CXCR4 levels and to modulate CXCL12-evoked cell migration, which can be extended to use of the arrestin-2/STAM-1 complex to identify and develop novel pharmacological agents capable of targeting the arrestin-2/STAM-1 interaction for therapeutic intervention. In a particular example, the arrestin-2/STAM-1 interaction may be blocked or otherwise disrupted, which can have therapeutically beneficial effects, for example, in the treatment of metastasis in cancer patients, and particularly cancers that have elevated levels of CXCR4 in the tumor cells.

Data obtained from investigations leading to the invention have indicated that the arrestin-2/STAM-1 complex serves to negatively regulate the cellular levels of CXCR4 upon activation with its cognate ligand (CXCL12), in other words, stabilizes CXCR4 levels in cells. In particular, interaction regions have been mapped between STAM-1 and arrestin-2 in both proteins, and over-expression of these regions in cells has been shown to disrupt the interaction and accelerate CXCR4 degradation. Over-expression of these regions has also been shown to inhibit CXCL12 evoked cell migration, while leaving signaling to extracellular regulated kinases 1 and 2 intact. As such, the arrestin-2/STAM-1 complex potentially represents a highly useful cellular target to decrease CXCR4 levels and to modulate cell migration by intentionally mediating the interaction between arrestin-2 and STAM-1, while leaving a subset of the intracellular signaling cascades and other functions of CXCR4 intact. As such, targeting the arrestin-2/STAM-1 complex may be particularly useful to inhibit migration of tumor cells, and thus metastasis, in patients who have cancers in which CXCR4 levels are elevated. The interface mediating the interaction between arrestin-2 and STAM-1 may be further useful as a target to develop and identify pharmacological agents that may disrupt the interaction between arrestin-2 and STAM-1, with the goal of using them as therapeutics to treat diseases in which reducing CXCR4 level/signaling and migration would be beneficial.

Prior art methods of modulating CXCR4 signaling have directly targeted CXCR4, thereby affecting all intracellular signaling pathways activated by CXCR4 and thus may have many unintended consequences. In contrast, the present invention targets the recently discovered arrestin-2/STAM-1 protein complex that shows specificity to a subset of CXCR4 related signaling and functional events. Therefore, another advantage of the invention is that side effects or unintended consequences are likely to be minimized by targeting the arrestin-2/STAM-1 complex. Also, by targeting the intracellular arrestin-2/STAM-1 complex, accelerated agonist-promoted degradation of CXCR4 occurs and cell migration can be inhibited. No other targets and/or agents that have this dual effect on CXCR4 degradation/migration are believed to be known. In addition, the capability to modulate both of these endpoints with a high degree of specificity would be particularly important outcomes for treating tumor metastasis.

The use of pharmacological agents that target the arrestin-2/STAM-1 complex may also be applicable to the treatment of other aspects related to cancer, such as tumor cell invasion, proliferation and angiogenesis. Additional potential uses of the arrestin-2/STAM-1 complex include the treatment of HIV/AIDS infection, WHIM (wart, hypogammaglobulinemia, infection, and myelokathexis) syndrome and opioid induced hyperalgesia. In each of these diseases, by targeting the arrestin-2/STAM-1 complex and enhancing CXCR4 degradation, decreased cellular levels of CXCR4 may reduce HIV infection, decrease CXCR4 signaling observed in WHIM syndrome patients and reduce pain in patients who suffer from opioid-induced hyperalgesia. In addition, targeting the arrestin-2/STAM-1 may be beneficial to treat highly metastatic cancers that are not CXCR4-dependent, such as those that have increased or amplified epidermal growth factor receptor expression.

Other potential therapeutic uses for targeting the arrestin-2/STAM-1 complex include the treatment of patients who suffer from cardiac and lung ischemia. Immediately after a cardiac ischemic event, cells in the heart release SDF-1α (the cognate ligand of CXCR4). Release of SDF-1α appears to mobilize progenitor cells in the bone marrow to travel to the ischemic site in the heart, where they initiate cardiac tissue repair in an attempt to restore cardiac function. The bone marrow-derived cells express CXCR4 and travel to the site of injury in response to the presence of SDF-1α released after the ischemic event. Increasing the mobilization of cells and improving their motility in response to SDF-1α could potentially increase the mobilization of bone marrow derived cells to the site of injury, with the potential for enhancing the repair mechanisms and benefiting individuals who suffer from cardiac ischemia following a heart attack. In that the invention identifies the arrestin-2/STAM-1 complex as a therapeutic target to modulate CXCR4 levels and CXCL12-evoked cell migration, a beneficial effect of enhancing the interaction may be the ability to improve cell mobility and increase the ability of bone marrow-derived progenitor cells to travel to the heart to initiate tissue repair. As such, while disrupting/blocking the arrestin-2/STAM-1 interaction is believed to be therapeutically beneficial for certain treatments, such as in the treatment of cancer, enhancing/promoting the interaction may be therapeutically beneficial as a treatment for cardiac ischemia.

Other aspects and advantages of this invention will be better appreciated from the following detailed description.

BRIEF DESCRIPTION OF THE DRAWINGS

In FIG. 1A, equimolar amounts (about 134 nM) of GST (glutathione S-transferase) immobilized on glutathione-Sepharose resin and GST-arrestin-2 were incubated with lysates from HEK293 cells transiently transfected with FLAG-STAM-1, FLAG-STAM-2 or FLAG-HRS. Bound proteins were detected by immunoblotting using the anti-FLAG M2 antibody. In FIG. 1B, equimolar amounts (about 117 nM) of GST-STAM-1, GST-STAM-2 and GST immobilized on glutathione-Sepharose resin were incubated with purified arrestin-2 (about 212 nM). Bound arrestin-2 was detected using an anti-arrestin-2 monoclonal antibody. In FIGS. 1A and 1B, blots were stripped and reprobed using an anti-GST antibody to determine the levels of the GST fusion proteins used in the binding assay. In FIG. 1C, lysates from HeLa cells either transiently transfected with HA-arrestin-2, HA-arrestin-3 or empty vector (pcDNA3) were incubated with antibodies to immunoprecipitate transfected as described below. Immunoprecipitates (IP) and lysates were analyzed by SDS-PAGE and immunoblotting as indicated.

In FIG. 2A, HeLa cells transiently transfected with HA-arrestin-2 were serum starved as described below, followed by treatment with 30 nM CXCL12 for about thirty to about sixty minutes. Cell lysates were subject to immunoprecipitation using monoclonal anti-HA and isotype control antibodies. Immunoprecipitates and lysates were analyzed by SDS-PAGE and immunoblotting to detect endogenous STAM-1 and HA-arrestin-2. Immunoblots were subject to densitometric analysis and the bar graph represents the average STAM-1 binding±S.E.M. normalized to the level of HA-arrestin-2 in the immunoprecipitates. STAM-1 binding to arrestin-2 was significantly increased upon agonist treatment as compared to vehicle. Data were analyzed by one-way ANOVA followed by a Bonferroni's post hoc test (*p<0.05). In FIG. 2B, STAM-1 is preferentially ubiquitinated upon CXCR4 activation. HEK293 cells co-transfected with HA-CXCR4, FLAG- STAM-1 or FLAG-STAM-2 and HA-ubiquitin were treated with 100 nM CXCL12 for 30 min. FLAG-STAM-1/2 were immunoprecipitated using an anti-FLAG antibody, followed by SDS-PAGE and immunoblotting to detect incorporated HA-ubiquitin. Blots were stripped and reprobed for FLAG-STAM-1/2 to assess loading. Cell lysates were analyzed for the presence of HA-CXCR4.

In FIG. 3A, serum-starved HEK293 cells expressing HA-CXCR4-YFP were treated with 30 nM CXCL12 or vehicle for about 30 minutes. Cells were fixed, permeabilized and double stained with anti-STAM-1 (red) and anti-EEAI (blue). White puncta in the merged images represents co-localization between all three proteins. The percent co-localization between CXCR4-YFP and STAM-1 was quantified as described below. The bar graph represents the percent co-localization between CXCR4-YFP and STAM-1 in vehicle and SDF treated cells±S.E.M. from 10 cells. Data were analyzed by Student t-test *$p<0.0001$. In FIGS. 3B, C and D, serum-starved HeLa cells were treated with about 30 nM CXCL12 or vehicle for about 30 minutes Cells were fixed, permeabilized and triple stained with anti-STAM-1 (green), anti-EEA1 (blue) and anti-CXCR4 (red) (FIG. 3B), triple stained with anti CXCR4 (red), anti-arrestin-2/3 (green) and anti-EEA1 (blue) (FIG. 3C); and HeLa cells expressing YFP-STAM-1 were double stained with arrestin-2/3 (red) and EEA1 (blue) (FIG. 3D). White puncta in the merged images represent co-localization between all three proteins. Co-localization between CXCR4 and STAM-1 (FIG. 3B; 20%), CXCR4 and arrestin (FIG. 3C; 30.7%), and YFP-STAM-1 and arrestin-2 (FIG. 3D; 26%). were quantified as described below. Inset represents 4-8× the size of the boxed region. DIC (differential interference contrast) images are shown.

FIG. 4 show data represent the mean±S.E.M. from three independent experiments, and illustrates that STAM-1 negatively regulates CXCR4 degradation. HEK293 cells stably expressing HA-CXCR4 were transfected with control (GAPD) and STAM-1 siRNA as described below. Cells were treated with vehicle (PBS containing about 0.01% BSA) or about 30 nM CXCL12 for about three hours and receptor levels were determined by immunoblotting followed by densitometric analysis. The bar graph represents the average amount of CXCR4 degraded±S.E.M. from three independent experiments (*$p<0.05$, unpaired t-test). In FIG. 4B, CXCR4 recycling was measured in HEK293 cells transfected with FLAG-CXCR4 and siRNA as described for FIG. 4A. Surface receptors were labeled with the M1 anti-FLAG antibody followed by treatment with about 30 nM of CXCL12 for about forty-five minutes in DMEM containing about 0.1% BSA, about 20 mM HEPES (pH 7.4) and about 1 mM Ca2+. Antibody remaining on the cell surface was stripped by two rapid washes with Ca2+/Mg2+ free PBS containing about 0.04% EDTA. Cells were then incubated in DMEM containing about 1 mM Ca2+ and about 10 μM AMD3100 (CXCR4 antagonist) and incubated at about 37° C. for about thirty to about sixty minutes. The amount of antibody reappearing on the cell surface was quantified by ELISA as described below, and used as an indicator of receptor recycling. Bars represent the percentage of internalized receptor that recycled±S.E.M. from three independent experiments. In FIG. 4C, bars represent the percentage of cell surface receptors internalized in cells treated with CXCL12 as compared with vehicle treated cells. The error bars represent S.E.M. from three independent experiments. In FIG. 4D, HeLa cells were transfected with GAPD and AMSH siRNA and treated and analyzed as in A.

In FIG. 5A, STAM-1 truncation mutants are represented schematically. Binding to GST-arrestin-2 is represented by (+) and (−) on the right as assessed by data shown in FIG. 11. In FIG. 5B, equimolar amounts (about 600 nM) of GST-arrestin-2 and GST were incubated with lysates from HEK293 cells transiently transfected with FLAG-tagged full-length-STAM-1 or STAM-1-ΔGAT. In FIG. 5C, equimolar amounts (about 117 nM) of GST-STAM-1-GAT and GST were incubated with lysates from HEK293 cells transiently transfected with FLAG-tagged arrestin-2. In FIGS. 5B and 5C, bound proteins were detected by immunoblotting, followed by staining blots with Ponceau-S to assess the amount of GST fusion protein used in the binding assay.

In FIG. 6A, Lysates from HeLa cells co-transfected with HA-arrestin-2 and FLAG-STAM-1-GAT (SI-GAT) or empty vector (PCMV) were incubated with anti-HA and IgG control antibodies. Immunoprecipitates were analyzed by immunoblotting to detect bound endogenous STAM-1 and lysates were analyzed to assess expression of the various constructs. FIG. 6A contains representative blots from one of three independent experiments. In FIG. 6B, HA-CXCR4 degradation was assessed in HEK293 cells expressing FLAG-STAM-1-GAT or empty vector (pCMV) as described below. FIG. 6C graphically represents the percent of receptor degraded. Error bars represent S.E.M. from three independent experiments. Data were analyzed by two-way ANOVA and followed by a Bonferroni's post hoc test. (*$p<0.0001$).

FIG. 7 contains representative blots from one of three independent experiments, and illustrates mapping of the STAM-1 binding domain on arrestin-2. FIG. 7A schematically represents arrestin-2 truncation mutants used in the binding studies. Binding between GST-STAM-1 and HA-tagged arrestin-2 truncation mutants is shown as weak (+), intermediate (++) and strong (+++) on the right of the graph. In FIG. 7B, equimolar amounts (about 234 nM) of GST-arrestin-2, GST-Arr2-(25-161) and GST were incubated with lysates from HEK293 cells transiently transfected with FLAG-tagged STAM-1 and empty vector (PCMV-10). In FIG. 7C, equimolar amounts (about 276 nM) of GST-STAM-1, GST-STAM-1-GAT and GST alone were incubated with lysates from HEK293 cells transiently transfected with FLAG-Arr-2-(25-161). In FIG. 7C, bound proteins were detected by immunoblotting using an anti-FLAG antibody and blots were stained with Ponceau-S to assess the amount of GST-tagged protein used in the binding assay.

In FIG. 8A, lysates were prepared from HeLa cells co-transfected with T7-STAM-1, HA-arrestin-2 and increasing amounts (about 0.1 μg and about 2.5 μg) of FLAG-Arr2 (25-161). Lysates were divided into equal aliquots and incubated with either an anti-T7 polyclonal antibody or protein G agarose alone (control). Immunoprecipitates were analyzed by immunoblotting to detect bound HA-arrestin-2 and endogenous HRS and lysates were analyzed to assess the expression of the various constructs. FIG. 8A shows representative blots from one of three independent experiments. In FIG. 8B, HA-CXCR4 degradation was assessed in HEK293 cells expressing FLAG-Arr2-(25-161)

or empty vector (PCMV) as described below. FIG. 8C is a graphical representation of percent receptor degraded. Error bars represent S.E.M. from three independent experiments. Data were analyzed by two-way ANOVA and followed by a Bonferroni's post hoc test. (*p<0.0001). Shown are representative blots from one of three independent experiments.

In FIGS. 9A and 9B, HEK293 cells stably expressing HA-CXCR4 were transfected with FLAG-ubiquitin and STAM-1-GAT domain or pCMV. In FIG. 9B, HeLa cells were transfected with HA-ubiquitin, T7-STAM-1 and STAM-1-GAT or pCMV. In FIG. 9C, cells were transfected as in FIG. 9A, except T7-HRS was also transfected. Cells were serum starved and treated with about 30 nM CXCL12 for about thirty to about sixty minutes, followed by immunoprecipitation and immunoblotting to detect incorporated ubiquitin as described below. Shown are representative blots from six (FIG. 9A) or three (FIGS. 9B and 9C) independent experiments.

FIGS. 12A and 12B represent equimolar amounts (about 117 nM) of GST-STAM-1 and GST immobilized on glutathione-Sepharose resin were incubated with lysates from HEK293 cells transiently transfected with HA-arrestin-2 constructs. Bound proteins were detected by immunoblotting using the anti-HA antibody, followed by staining with Ponceau-S to assess the amount of GST fusion proteins used in the binding assay. Shown are representative blots from one of three independent experiments.

FIG. 14 contains a table identifying primers used for generating DNA constructs used in investigations leading to the present invention.

DETAILED DESCRIPTION OF THE INVENTION

Figure 1:
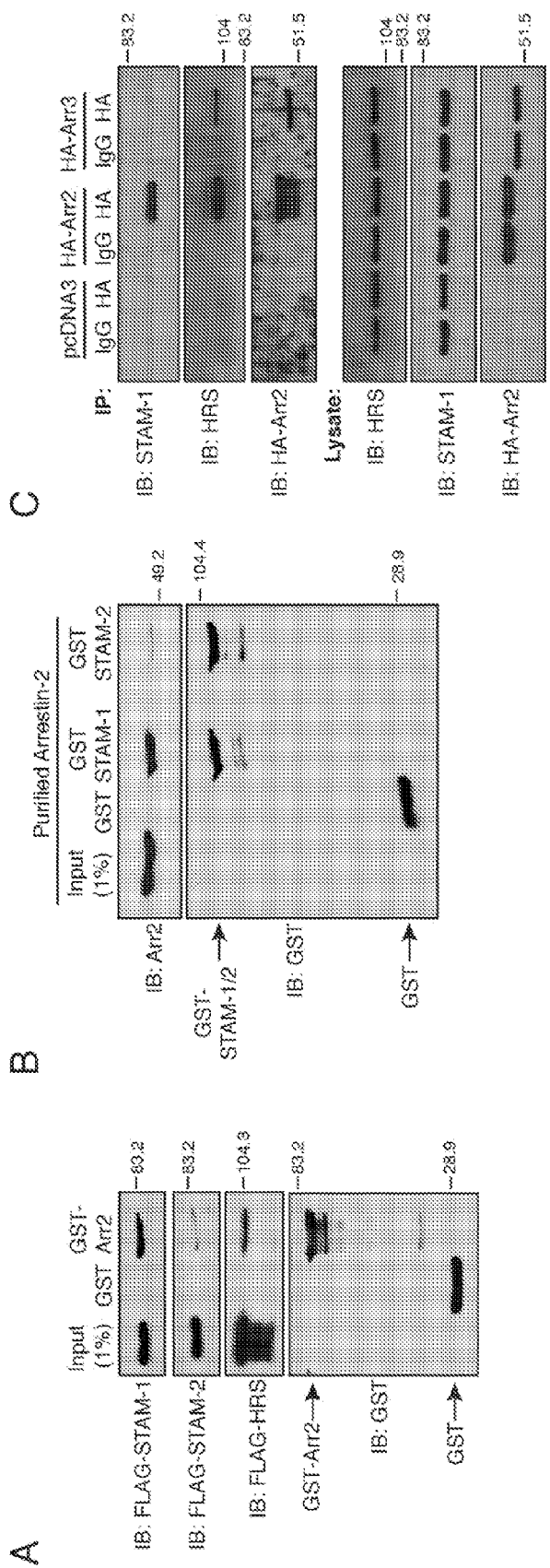
FIG. 1 contains representative blots from one of three (FIG. 1A-FIG. 1C) independent experiments, and illustrates interactions between arrestin-2 and ESCRT-0.

The chemokine receptor CXCR4, a G protein-coupled receptor, is targeted for lysosomal degradation via a ubiquitin-dependent mechanism that involves the endosomal sorting complex required for transport (ESCRT) machinery. The following reports an investigation which showed that arrestin-2 interacts with ESCRT-0, a protein complex that recognizes and sorts ubiquitinated cargo into the degradative pathway. In particular, STAM-1 (but, notably, not related STAM-2) interacts directly with arrestin-2 and co-localizes with CXCR4 on EEA1 positive early endosomes. Depletion of STAM-1 by RNAi and disruption of the arrestin-2/STAM-1 interaction accelerates agonist-promoted degradation of CXCR4, suggesting that STAM-1 via its interaction with arrestin-2 negatively regulates CXCR4 endosomal (lysosomal) sorting via ubiquitination of HRS. The investigation provided mechanistic insight into the role that arrestin-2 has on targeting CXCR4 into the degradative pathway and furthered an understanding of the complex molecular events that mediate endosomal sorting of GPCRs. Interestingly, disruption of the STAM-1/arrestin-2 interaction blocks agonist-promoted ubiquitination of HRS, but not CXCR4 and STAM-1 ubiquitination. Data from the investigation described below suggest a mechanism whereby arrestin-2, via its interaction with STAM-1, is able to modulate CXCR4 sorting by regulating the ubiquitination status of HRS.

Provided below are descriptions of materials and methods utilized in the investigation.

The following cell lines, antibodies and reagents were obtained and used in the investigation. HEK (Human embryonic kidney) 293 cells (obtained from Microbix of Toronto, Canada) and HeLa cells (American Type Culture Collection) were maintained in a Dulbecco's modified Eagles medium (DMEM; Hyclone) supplemented with 10% fetal bovine serum (FBS; HyClone Laboratories, Logan, Utah USA). HRS (M-79) rabbit polyclonal, the β-arrestin1/2 rabbit polyclonal (H-290) and mouse monoclonal (21-B1) antibodies were obtained from Santa Cruz Biotechnology (Santa Cruz, Calif. USA). Anti-GST monoclonal antibody and gluthathione Sepharose 4B resin were obtained from GE Healthcare (Buckinghamshire, UK). Anti-CXCR4 antibody previously described in Marchese and Benovic (2001). STAM-1 and AMSH polyclonal antibodies were obtained from ProteinTech Group (Chicago, Ill. USA). Arrestin-2 and anti-EEA1 monoclonal antibodies were obtained from BD Biosciences (San Jose, Calif. USA). Anti-HA polyclonal and monoclonal antibodies were obtained from Covance (Berkeley, Calif. USA). Anti-FLAG M2, M1, and M2-horse radish peroxidase conjugated monoclonal antibodies, FLAG polyclonal antibody, Alkaline Phosphatase conjugated anti-mouse antibody, and AMD3100 were obtained from Sigma (St. Louis, Mo. USA). An alkaline phosphatase substrate kit was obtained from Bio-Rad (Hercules, Calif. USA). Anti-T7 goat polyclonal antibody was obtained from Abcam (Cambridge, Mass. USA). Anti-epidermal growth factor receptor mouse monoclonal antibody was obtained from StressGen (Ann Arbor, Mich. USA). Anti-actin monoclonal antibody was obtained from MP Biomedicals (Aurora, Ohio USA). Stromal cell-derived factor-1α (CXCL12) and epidermal growth factor were obtained from PeproTech (Rockyhill, N.J. USA). Alexa-Fluor 635-conjugated goat anti-mouse, Alexa-Fluor 594-conjugated anti-rat, Alexa-Fluor 488-conjugated goat anti-rabbit and Alexa-Fluor 568-conjugated goat anti-rabbit antibodies were obtained from Molecular Probes (Eugene, Oreg. USA). The siRNA for GAPD, STAM-1 (GAAC-GAAGAUCCGAUGUAU) and AMSH (siGENOME SMARTpool D-012202) were obtained from Dharmacon RNA Technologies (Lafayette, Colo. USA).

The following DNA constructs obtained and used in the investigation were HA-CXCR4, FLAG-ubiquitin, HA-CXCR4-YFP, HA-arrestin-3 and HA-arrestin-2 constructs, as previously described in (Bhandari et al., 2007). Primers used for generating all constructs are listed in a table attached hereto as FIG. 14. For STAM-1 truncation mutants (1-195, 1-269, 1-390, 391-540, 337-540, 270-540, 212-540, 144-540), full-length STAM-1 in 3xFLAG-pCMV-10 was amplified by PCR using primers flanking various regions of STAM-1 as indicated above and harboring 5' and 3' HindIII and XbaI restriction enzyme sites, respectively. PCR fragments were digested and ligated into the HindIII and XbaI sites of 3x-FLAG pCMV-10 (Sigma). For STAM-1-ΔGAT, the region encompassing amino acid residues 343-377 was deleted by two-step PCR with mutually annealing overlapping primers and flanking primers based on 3xFLAG-pCMV-10. Amplified product was digested and ligated into HindIII and XbaI sites of 3xFLAG-pCMV-10 and pGEX-4T2 (GE Healthcare). For STAM-1-GAT, amino acid residues 296-380 were amplified by PCR from full-length FLAG-STAM-1 and cloned into the HindIII and XbaI sites of 3xFLAG-pCMV-10 and EcoRI and XhoI sites of pGEX-4T2. For arrestin-2-(25-161) constructs, amino acid residues 25-161 were amplified by PCR from HA-arrestin-2-(1-161) and cloned into HindIII and XbaI sites of 3xFLAG pCMV-10 and SmaI and XhoI sites of pGEX-4T2, respectively. For YFP-STAM-1, full-length STAM-1 was amplified from FLAG-STAM-1 and cloned into the HindIII and KpnI sites of pEYFP-C1 vector (Clontech, Mountain View, Calif.). The sequence of all constructs was verified by sequencing.

The following GST-fusion protein binding assays were obtained and used in the investigation. *Escherichia coli* BL21 cells transformed with GST-fusion protein constructs or empty vector (pGEX-4T2) were grown overnight in Luria Broth (LB) containing about 100 μg/ml ampicillin. The following day, cultures were diluted (about 3.7%) and grown to an $OD_{600}$ of about 0.35 to about 0.40 at about 37° C., followed by induction with about 0.1 mM IPTG (isopropyl-1-thio-β-$_D$-galactopyranoside) for about one hour at about 18° C. Cells were then pelleted by centrifugation and resuspended in about 1 mL binding buffer (about 20 mM Tris-Cl (pH 7.4), about 150 mM NaCl, about 0.1% Triton X-100, about 1 mM dithiothreitol, about 10 μg/ml leupeptin, about 10 μg/ml aprotinin, about 10 μg/ml pepstatin-A), followed by sonication and centrifugation. Clarified lysates were incubated with glutathione-Sepharose 4B resin for about one hour, washed and resuspended in binding buffer. Samples were analyzed by SDS-PAGE and stained with Gel-Code blue to estimate the protein amounts by comparing the samples to known amounts of purified bovine serum albumin (Roche, Fraction V). For binding assays, equimolar amounts of purified GST-fusion proteins were incubated with about 100 μl clarified cell lysate of HEK293 cells expressing the desired construct for about two to about four hours at about 4° C. For binding experiments using purified arrestin-2, GST fusion proteins were incubated with about 500 ng arrestin-2 in about 100 μl binding buffer for about one hour at about 4° C. Following incubation, samples were washed three times with binding buffer, eluted in 2x sample buffer by boiling for about 10 minutes, and bound proteins were detected by SDS-PAGE followed by immunoblotting.

The following degradation assay was obtained and used in the investigation. HEK293 cells stably expressing HA-CXCR4 or HeLa cells expressing endogenous levels of CXCR4 grown on 10-cm dishes were transfected with about 100 nM STAM-1, AMSH or GAPD siRNA using Lipofectamine 2000 transfection reagent (Invitrogen of Carlsbad, Calif. USA). To assess the role of STAM-1 and arrestin-2 minigene constructs on CXCR4 degradation, HEK293 cells grown on 10-cm dishes were co-transfected with about 1 μg HA-CXCR4 and about 9 μg FLAG-STAM-1-GAT, FLAG-arrestin-2-(25-161) or empty vector (pCMV-10) using TransIT-LTI transfection reagent (Mirus of Madison, Wis. USA). About twenty-four hours later, cells were passaged onto poly-L-lysine (about 0.1 mg/ml, Sigma) coated 24-well plates (HEK293 cells) or 6 well plates (HeLa cells) and grown for an additional eighteen to twenty-four hours. Cells were washed once and incubated with DMEM containing about 10% FBS and about 50 μg/ml cycloheximide to stop protein synthesis for about fifteen minutes at about 37° C. Cells were then incubated with the same medium-containing vehicle (about 0.5% BSA) or about 30 nM CXCL12 for about one, two and three hours. Cells were washed and collected in about 300 μl 2x sample buffer, sonicated and receptor amounts were determined by SDS-PAGE followed by immunoblotting using an anti-HA monoclonal antibody or anti-CXCR4 antibody, as previously described (Marchese, A., Ubiquitination of chemokine receptors, Methods Enzymol, 460, 413-422 (2009). To assess EGFR degradation, HeLa cells grown on six well plates were transfected with about 3 μg FLAG-STAM-1-GAT, FLAG-arrestin-2-(25-161) or empty vector (pCMV-10) using TransIT-LT1 transfection reagent. Forty-eight hrs following transfection cells were incubated with DMEM containing 10% FBS and 50 μg/ml cycloheximide to stop protein synthesis for 15 min at about 37° C. Cells were then incubated with the same medium containing vehicle (0.5% BSA) or 100 ng/ml EGF for 1 hr. Cells were processed as described above for CXCR4 degradation.

The following coimmunoprecipitation studies were used in the investigation. HeLa cells were transiently transfected with HA-Arrestin-2, HA-arrestin-3 or empty vector alone (pcDNA3) using TransIT-LT1 transfection reagent. About forty-eight hours later, cells were collected in an approximately 1.5 mL immunoprecipitation buffer (about 20 mM $Na_2PO_4$ (pH 6.5), about 150 mM NaCl, about 1% (v/v) Triton-X 100, about 10 μg/ml leupeptin, about 10 μg/ml aprotinin, about 10 μg/ml pepstatin A) and incubated at about 4° C. for about thirty minutes. Cells were sonicated, centrifuged and clarified lysates were incubated with an anti-HA monoclonal antibody or isotype control antibody to immunoprecipitate HA-tagged arrestin-2/3 followed by immunoblotting to detect bound endogenous STAM-1 and HRS. Endogenous arrestins were immunoprecipitated from HeLa cells using an anti-arrestin2/3 mouse monoclonal or isotype control antibody followed by immunoblotting to detect bound endogenous STAM-1 and HRS. To assess the effect of the STAM-1-GAT minigene on the interaction between STAM-1 and arrestin-2, lysates from HeLa cells transfected with HA-arrestin-2 and FLAG-STAM-1-GAT or pCMV were incubated with an anti-HA or isotype control antibody and immunoprecipitates were analyzed for the presence of endogenous STAM-1. To assess the effect of the arrestin-2-(25-161) minigene on the interaction between STAM-1 and arrestin-2, HeLa cells transfected with T7-STAM-1, HA-arrestin-2 and FLAG-arrestin-2-(25-161) or pCMV were incubated with an anti-T7 polyclonal antibody and immunoprecipitates were analyzed for the presence of HA-arrestin-2 and endogenous HRS.

The following confocal Immunofluorescence microscopy techniques were used in the investigation. HEK293 cells transiently transfected with HA-CXCR4-YFP were passaged onto poly-L-lysine coated coverslips and allowed to grow for about twenty-four hours. HeLa cells were used to examine the distribution of endogenous CXCR4. Cells were washed once with warm DMEM containing about 20 mM HEPES (pH 7.5) and incubated in the same medium for about three to about four hours at about 37° C. Cells were treated with about 30 nM CXCL12 or vehicle for about thirty minutes, fixed with about 3.7% paraformaldehyde and then permeabilized with about 0.05% (w/v) saponin for about ten minutes, similar to a protocol previously described in Bhandari et al. (2007). Cells were co-incubated with STAM-1, EEA1 or arrestin2/3 antibodies. Endogenous CXCR4 in HeLa cells was stained with rat anti-CXCR4 monoclonal antibody. Briefly, after permeabilization and fixation, cells were incubated with about 1% BSA in about 0.05% saponin-PBS for about thirty minutes at about 37° C., followed by incubating with primary antibody for about one hour at about 37° C. Primary antibodies for STAM-1 and EEA1 were used at about 1:100 dilution and against CXCR4 and arrestin2/3 was used at an approximately 1:50 dilution. Cells were washed five times with 0.05% saponin-PBS, followed by incubating with appropriate Alexa-Fluor conjugated secondary antibodies for about thirty minutes at about 37° C. Finally cells were washed with PBS and fixed again with about 3.7% formaldehyde-PBS, and then mounted onto glass slides using mounting media containing DAPI. Samples were analyzed using a Zeiss LSM 510 laser scanning confocal microscope equipped with a Plan-Apo 63×/1.4 oil lens objective. Images were acquired using a 1.4 megapixel cooled extended spectra range RGB digital camera set at 512×512 resolution. Acquired images were analyzed using ImageJ software (version 1.41o) and the amount of co-localization between proteins was determined using the colocalization plug-in feature of MAG Biosystems Software (7.6.2.0).

The following ubiquitination assays were obtained and used in the investigation. For CXCR4 ubiquitination, HEK293 cells stably expressing HA-CXCR4 grown on 10-cm dishes were transfected with about 3 µg FLAG-ubiquitin. About eight hours later, cells were transfected either with about 10 µg FLAG-STAM-1-GAT, FLAG-Arr2-(25-161) or empty vector (pCMV). The next day, cells were passaged onto 6-cm dishes and allowed to grow for an additional twenty-four hours. The following day, cells were serum starved in DMEM containing about 20 mM HEPES for about three hours and then treated with about 30 nM SDF for about thirty minutes, washed once on ice with cold PBS and collected in an approximately 1 mL lysis buffer (about 50 mM Tris-Cl (pH 7.4), about 150 mM NaCl, about 5 mM EDTA, about 0.5% (w/v) sodium deoxycholate, about 1% (v/v) NP-40, about 0.1% (w/v) SDS, about 20 mM NEM, about 10 µg/ml each of leupeptin, aprotinin and pepstatin A). Samples were transferred into microcentrifuge tubes and placed at about 4° C. for about thirty minutes, sonicated, followed by centrifugation to pellet cellular debris. Clarified cell lysate was incubated with an anti-HA polyclonal antibody and the immunoprecipitates were analyzed by SDS-PAGE followed by immunoblotting using an anti-FLAG antibody conjugated to HRP.

To detect HRS ubiquitination, HEK293 cells stably expressing HA-CXCR4 were transfected with about 3 µg FLAG-ubiquitin. About eight hours later cells, were co-transfected with about 8 µg FLAG-STAM-1-GAT or empty vector (pCMV-10) and about 2 µg T7-tagged HRS. About twenty-four hours later, cells were passaged onto poly-L-lysine coated 6-cm dishes and the next day cells were serum starved for about four to about five hours in DMEM containing about 20 mM HEPES and were treated with about 30 nM SDF or vehicle alone for about thirty to about sixty minutes. Cells were washed with cold PBS and collected in an approximately 1 ml ubiquitination buffer (about 20 mM Tris-Cl (pH 7.5), about 150 mM NaCl, about 1% Triton-X 100, about 5 mM EDTA, about 20 mM NEM, about 10 µg/ml leupeptin, about 10 µg/ml aprotinin and about 10 µg/ml pepstatin-A), incubated for about thirty minutes at about 4° C., sonicated and clarified by centrifugation. HRS was immunoprecipitated using an anti-HRS polyclonal antibody and immunoprecipitates were analyzed by SDS-PAGE followed by immunoblotting to detect ubiquitinated HRS using an anti-FLAG antibody conjugated to HRP.

For STAM-1 ubiquitination experiments, HeLa cells grown in 6-well dishes were co-transfected with about 3 µg T7-STAM-1 and about 40 ng HA-ubiquitin. About eight hours later, cells were transfected with about 3 µg FLAG-STAM-1-GAT or empty vector (pCMV-10). About twenty-four hours later, cells were passed onto poly-L-lysine coated 6-cm dishes and the following day cells were serum starved, treated and processed as described above for HRS ubiquitination using a modified ubiquitination buffer (about 20 mM $Na_2PO_4$ (pH 6.5), about 150 mM NaCl, about 1% Triton-X 100, about 20 mM NEM and protease inhibitor cocktail). Tagged STAM-1 was immunoprecipitated using an anti-T7 goat polyclonal antibody and immunoprecipitates were analyzed by SDS-PAGE followed by immunoblotting to detect ubiquitinated STAM-1 using an anti-HA monoclonal antibody.

The following internalization and recycling assays were obtained and used in the investigation. For measuring internalization and recycling of CXCR4, HEK293 cells grown on 10-cm dishes were co-transfected with FLAG-CXCR4 (about 1 µg) and about 100 nM STAM-1 or GAPD siRNA using Lipofectamine 2000 transfection reagent. The next day, cells were passaged onto poly-L-lysine coated 24-well plates and grown for an additional twenty-four hours. Cells were serum starved for about three to about four hours, placed on ice, washed once with DMEM containing about 0.1% BSA, about 20 mM HEPES and about 1 mM Ca2+ and then incubated in the same medium containing the calcium-dependent MI anti-FLAG antibody for about one hour on ice, which labels cell surface receptors only. Cells were washed and incubated in the same medium containing vehicle or about 30 nM CXCL12 for about forty-five minutes at about 37° C. To remove surface bound antibody, cells were washed three times with Ca2+ and Mg2+-free PBS containing about 0.04% EDTA. Cells were incubated in DMEM containing about 1 mM Ca2+ and the CXCR4 antagonist AMD3100 (about 10 µM) to block any further internalization for about thirty to about sixty minutes at about 37° C. The amount of receptor/antibody that recycled back to the cell surface was quantified by incubating cells with an alkaline-phosphatase conjugated goat anti-mouse IgG antibody. Briefly, cells were washed once with PBS containing about 1 mM Ca2+ and then fixed with about 3.7% paraformaldehyde for about five minutes on ice. Following fixation, cells were washed three times and incubated with alkaline phosphatase conjugated goat anti-mouse antibody diluted in PBS containing about 1% BSA for one hour at room temperature. Cells were then washed with PBS and incubated with p-nitrophenyl phosphate diluted in diethanolamine buffer (Bio-Rad) for about five to about fifteen minutes. Reactions were stopped by adding about 0.4 N NaOH and an aliquot was used to measure the absorbance at 405 nm. Percent receptor recycling was calculated by dividing the amount of receptor internalized by the amount of receptors recovered after incubation at different time intervals. To calculate the percent receptor internalization, the amount of receptor remaining on the cell surface was divided by the total number of receptors present on the cell surface before treatment with agonist.

Statistical analyses performed in the investigation used GraphPad Prism 4.00 for Macintosh (GraphPad Software, San Diego, Calif.; www.graphpad.com).

The following describes results that were obtained with the investigation. A first phase of the investigation established that arrestins interact with ESCRT-0. Although it has been previously shown that HRS and arrestin-2 mediate endosomal sorting of CXCR4 into the degradative pathway (Marchese et al., 2003; Bhandari et al., 2007), the molecular mechanisms have remained poorly understood. To gain mechanistic insight into this process, the investigation initially examined whether arrestin-2 interacts with ESCRT-0 by determining if it binds to HRS, STAM-1 or STAM-2. To address this, celilysates prepared from HEK293 cells expressing FLAG-tagged STAM-1, STAM-2 or HRS were incubated with bacterially purified GST-arrestin-2 and GST immobilized on glutathione-Sepharose resin. As shown in FIG. 1A, arrestin-2 bound to STAM-1 and HRS, but only weakly to STAM-2. To rule out the possibility of an intermediate protein mediating the interaction with STAM-1, similar experiments were performed using purified arrestin-2. As shown in FIG. 1B, GST-STAM-1, but not GST-STAM-2 or GST, bound to purified arrestin-2, which indicated that the interaction between arrestin-2 and STAM-1 is direct and confirming that arrestin-2 binds poorly to STAM-2. To determine whether arrestin-2 associates with ESCRT-0 in cells, HA-arrestin-2, HA-arrestin-3 or empty vector (pcDNA3) were transfected into HeLa cells followed by immunoprecipitation and immunoblotting to detect the presence of endogenous STAM-1 and HRS. Both STAM-1 and HRS were detected in the immunoprecipitates from cells expressing HA-arrestin-2, suggesting that arrestin-2 associates with HRS and STAM-1 in cells (FIG. 1C), while HRS, but not STAM-1, was detected in the HA-arrestin-3 immunoprecipitates (FIG. 1C). Similarly, endogenous arrestins also co-immunoprecipitated with endogenous STAM-1 and HRS in HeLa cells. Taken together, these data showed that the interaction between STAM-1 and non-visual arrestins is limited to arrestin-2, and that HRS interacts with both arrestin-2 and arrestin-3. Additionally, the data suggested that arrestin-2 exists in complex with a subpopulation of ESCRT-0 that includes STAM-1 and HRS, but not STAM-2.

Figure 2:
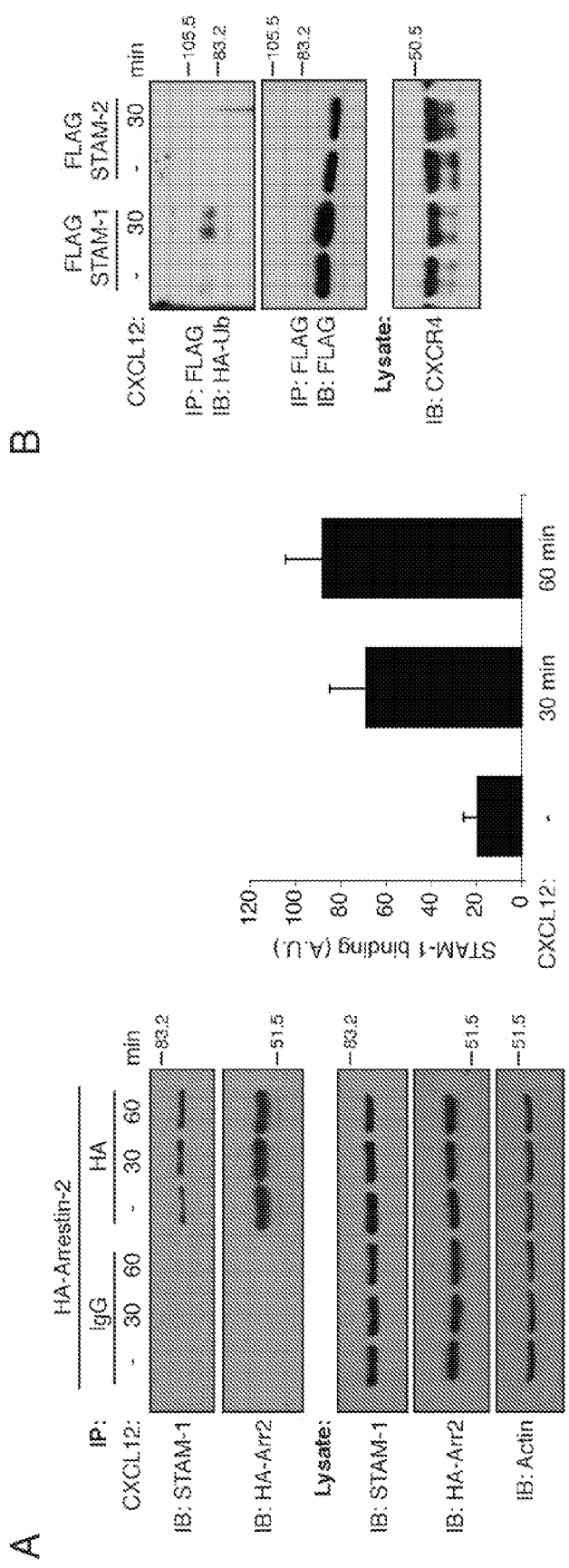
FIG. 2 contains representative blots from one of three independent experiments, and illustrates the regulation of the arrestin-2/STAM-1 interaction with CXCR4.

The investigation then examined whether the interaction between arrestin and ESCRT-0 was regulated by activation of CXCR4. HeLa cells, which endogenously express CXCR4, were transfected with HA-arrestin-2 and treated with CXCL12 (about 30 nM) or vehicle (about 0.05% BSA-PBS) for various times, followed by immunoprecipitation of tagged arrestin-2 and immunoblotting to detect bound endogenous STAM-1. Activation of CXCR4 enhanced the interaction between STAM-1 and arrestin-2 as early as about thirty minutes after agonist treatment that persisted up to about sixty minutes (FIG. 2A). As STAM has been shown to be ubiquitinated (McCullough et al., 2004), the investigation next assessed whether CXCR4 activation promotes ubiquitination of STAM-1. HEK293 cells transfected with FLAG-tagged STAM-1 or STAM-2 and HA-tagged ubiquitin were treated with CXCL12 (about 100 nM) for about thirty minutes, followed by immunoprecipitation of tagged STAM proteins and immunoblotting to detect incorporation of tagged ubiquitin. As shown in FIG. 2B, STAM-1 was ubiquitinated by agonist activation of CXCR4, whereas STAM-2 was not ubiquitinated.

To confirm that arrestin-2 and STAM-1 are found within the same intracellular compartment, the investigation examined their distribution in cells by confocal immunofluorescence microscopy. As shown in FIG. 3A, in HEK293 cells transfected with YFP-tagged CXCR4 (a construct previously described in Bhandari et al., 2009), CXCR4 was mainly localized to the plasma membrane in vehicle-treated cells, whereas endogenous STAM-1 was mainly localized to punctate vesicles distributed throughout the cytoplasm, many of which also co-localized with EEA1, used here as a marker for early endosomes. In contrast, upon agonist treatment, CXCR4 distributed into an intracellular punctate pattern, indicating that it had internalized into vesicles that also contained STAM-1 and EEA1 (FIG. 3A, bottom panels). The distribution of endogenous CXCR4 in HeLa cells treated with CXCL12 was also examined for about thirty minutes, revealing that CXCR4 co-localized with endogenous STAM-1 (FIG. 3B) and arrestin-2/3 (FIG. 3C) on EEA1 positive early endosomes. CXCR4 activation also promoted co-localization of arrestin-2/3 and YFP-tagged STAM-1 on early endosomes in HeLa cells (FIG. 3D). Taken together, the data suggested that, upon internalization, CXCR4 appears on early endosomes together with arrestin-2 and STAM-1.

As the data suggest that STAM-1 has a role in endosomal sorting of CXCR4, the investigation then examined agonist-promoted degradation of CXCR4 in cells that were depleted of STAM-1 by RNA interference. HEK293 cells stably expressing HA-CXCR4 were transfected with control or STAM-1 siRNA, followed by treatment with CXCL12 (about 30 nM) for about three hours and receptor degradation was assessed by immunoblot analysis, as previously described in Marchese et al. (2003). As shown in FIG. 4A, siRNA mediated depletion of STAM-1 led to a moderate, but statistically significant, increase in CXCR4 degradation, as compared to control siRNA treated cells, suggesting that STAM-1 negatively regulates agonist-promoted degradation of CXCR4. As the amount of receptor that is degraded is in part a function of the rate of receptor internalization and recycling, the effect of depleting STAM-1 on CXCR4 internalization and recycling was also examined. Cell surface FLAG-tagged CXCR4 was labeled with the M1 anti-FLAG antibody on ice in the presence of about 1 mM $Ca^{2+}$, as the M1 antibody binds to the FLAG epitope in a calcium-dependent manner. Cells were washed to remove unbound antibody and the media was replaced with DMEM containing CXCL12 (about 30 nM) in the continued presence of about 1 mM $Ca^{2+}$ and placed at about 37° C. for forty-five minutes to allow for internalization of the M1/CXCR4 complexes to take place. Antibody remaining on the surface, mostly representing un-internalized receptor, was removed by incubating cells with PBS containing EDTA (about 0.04%), a calcium-chelating agent. The amount of antibody (receptor) that recycled back to the cell surface was quantified by cell surface ELISA in parallel wells that were incubated at about 37° C. for about thirty to about sixty minutes. In control siRNA treated cells, approximately 20% of internalized CXCR4 recycled back to the cell surface after about thirty to about sixty minutes, similar to what was observed in STAM-1 depleted cells, suggesting that STAM-1 depletion had no effect on recycling of CXCR4 (FIG. 4B). In addition, agonist-promoted internalization of CXCR4 was similar in STAM-1 depleted cells, as compared to control siRNA treated cells, suggesting that STAM-1 is not involved in CXCR4 internalization (FIG. 4C).

The role of AMSH on agonist-promoted degradation of CXCR4 was also examined. AMSH is a deubiquitinating enzyme that interacts with STAM-1 and negatively regulates endosomal sorting of the epidermal growth factor receptor (EGFR) (see McCullough et al., (2004)). As shown in FIG. 4D, siRNA mediated depletion of AMSH did not affect agonist-promoted degradation of CXCR4 in HeLa cells, suggesting that AMSH does not regulate endosomal sorting of activated CXCR4. However, CXCR4 levels were elevated in vehicle-treated cells transfected with AMSH siRNA (FIG. 4D), suggesting that AMSH may regulate degradation of constitutively internalized CXCR4, similar to what has been recently reported in (Sierra, M. I., Wright, M. H., and Nash, P., AMSH interacts with ESCRT-0 to regulate the stability and trafficking of CXCR4, J. Biol. Chem., jbc.M109.061309, First Published on Feb. 16, 2010, doi: 10.1074/jbc.M109.061309 (2010). Taken together, the data suggested that STAM-1 negatively regulates CXCR4 degradation likely through a mechanism that directly attenuates endosomal sorting.

Figure 5:
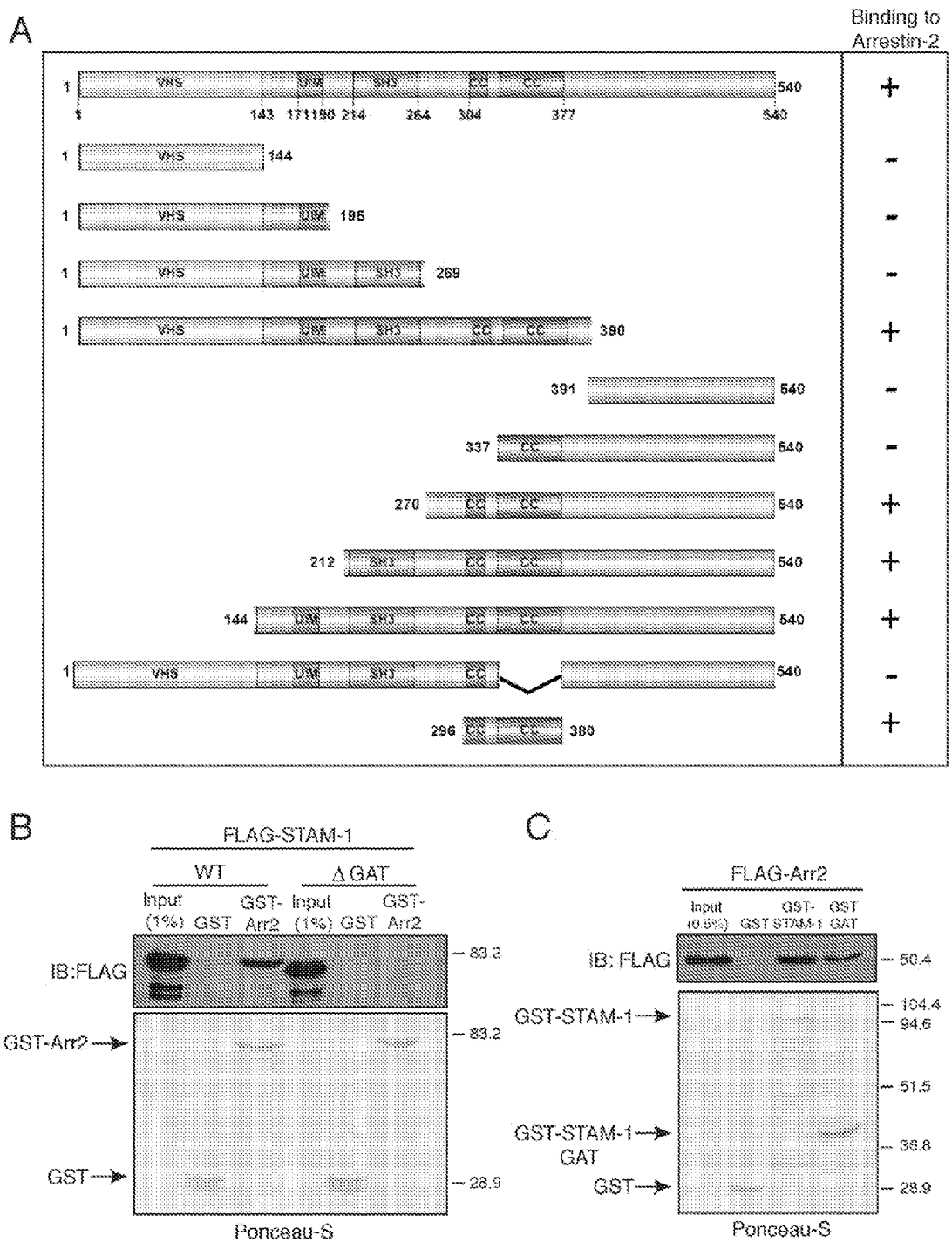
FIG. 5 contains representative blots from one of three independent experiments, and illustrates that the STAM-1 GAT domain is both necessary and sufficient for arrestin-2 binding.
Figure 11:
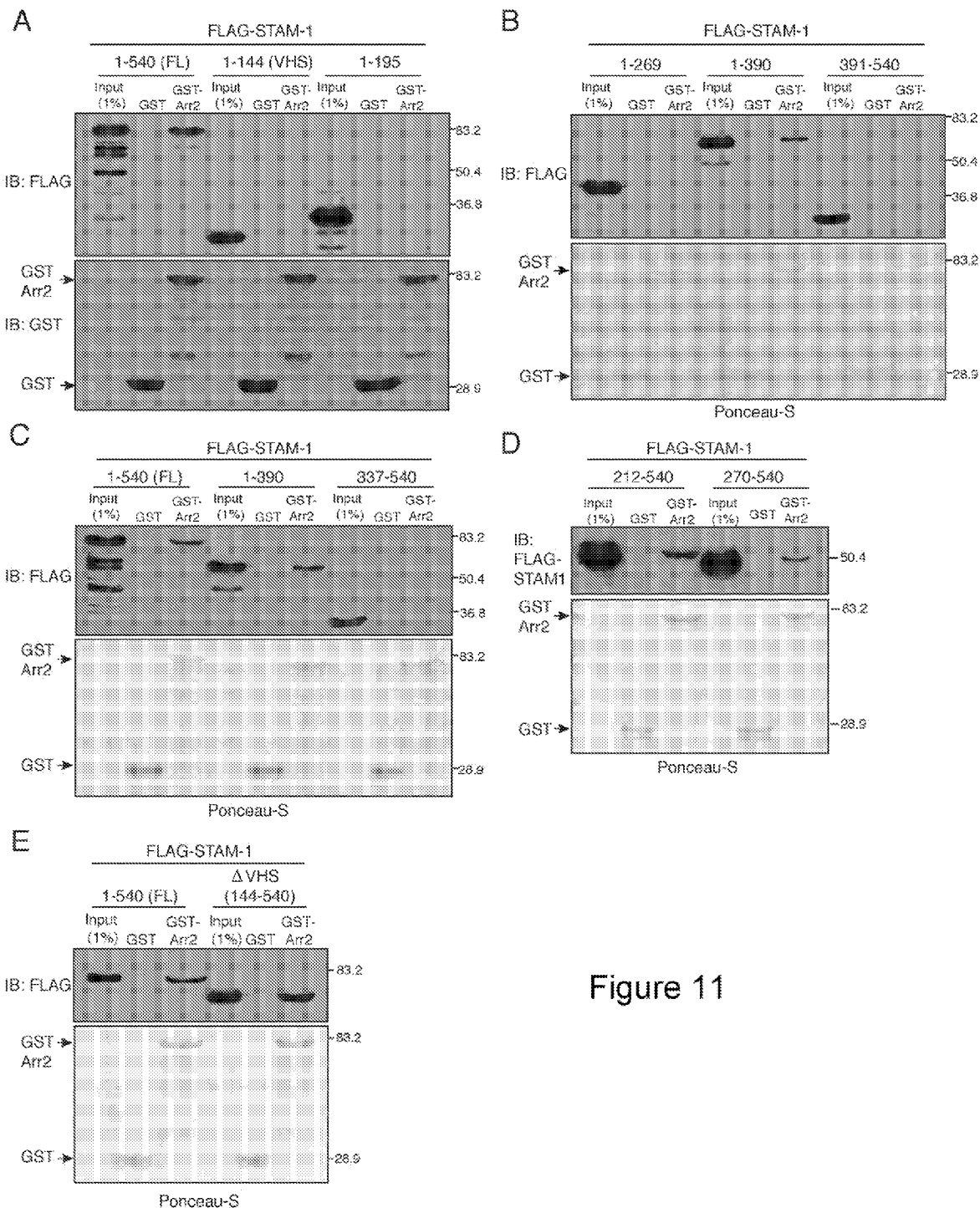
FIGS. 11A through 11E represent equimolar amounts (about 134 nM) of GST-arrestin-2 and GST immobilized on glutathione-Sepharose resin were incubated with lysates from HEK293 cells transiently transfected with various FLAG-STAM-1 constructs. Bound proteins were detected by immunoblotting using the anti-FLAG M2 antibody, followed by staining with Ponceau-S (FIGS. 11B-E) or immunoblotting for GST (FIG. 11A) to assess the amount of GST fusion proteins used in the binding assays. Shown are representative blots from one of three independent experiments.

The investigation then turned to examining the arrestin-2 binding site on STAM-1. Arrestin-2 was recently reported to positively regulate CXCR4 sorting into the degradative pathway. To gain insight into the function of the arrestin-2/STAM-1 interaction on CXCR4 trafficking, the investigation initially set out to determine the mechanism of the interaction. To accomplish this, the investigation mapped the arrestin-2 binding region on STAM-1 by truncation mutagenesis. STAMs contain multiple domains, characterized by the presence of an amino-terminal VHS domain (Vps27, Hrs, STAM homology), UIM (ubiquitin interacting motif), SH3 (Src homology) domain, ITAM (immunoreceptor based tyrosine activation motif) and a GAT (GGA and TOM1 homologous) domain that partially overlaps with the ITAM (Prag, G., Watson, H., Kim, Y. C., Beach, B. M., Ghirlando, R., Hummer, G., Bonifacino, J. S., and Hurley, J. H., The Vps27/Hse1 complex is a GAT domain-based scaffold for ubiquitin-dependent sorting, Dev. Cell 12, 973-986 (2007); Ren, X., Koer, D. P., Kim, Y. C., Ghirlando, R., Saidi, L. F., Hummer, G., and Hurley, J. H., Hybrid structural model of the complete human ESCRT-0 complex, Structure 17, 406-416 (2009). Several STAM-1 N-terminal and C-terminal truncation mutants were created according to its domain organization, tagged with the FLAG epitope on the amino terminal end (FIG. 5A). GST-arrestin-2 and GST immobilized on glutatruone-Sepharose resin were incubated with lysates expressing the various STAM-1 truncation mutants and bound proteins were detected by immunoblotting. The results from these experiments are summarized in FIG. 5A and the data are shown in FIG. 11. The arrestin-2 binding region was determined to reside between amino acid residues 296-380 on STAM-1. This region encompasses the GAT domain, which has been shown to form two tandem coiled-coil domains (amino-acid residues 301-377) (Prag et al., 2007; Ren et al., 2009). To further confirm that the GAT domain mediates binding to arrestin-2, deletion of the GAT domain completely abrogated STAM-1 binding to arrestin-2 (FIG. 5B) and the GAT domain alone fused to GST was able to bind to arrestin-2 (FIG. 5C).

To determine if the interaction between STAM-1 and arrestin-2 is important for CXCR4 trafficking, the investigation initially expressed the GAT domain as a minigene in cells and assessed whether it disrupted the arrestin-2/STAM-1 interaction. HeLa cells transfected with FLAG-SI-GAT and HA-arrestin-2 were subjected to immunoprecipitation using an anti-HA antibody followed by immunoblotting to detect the presence of endogenous STAM-1 in the immunoprecipitates. As shown in FIG. 6A, expression of the GAT domain disrupted the arrestin-2/STAM-1 interaction. To determine the function of the arrestin-2/STAM-1 interaction on lysosomal targeting of CXCR4, the investigation examined the effect of expressing the GAT domain on CXCR4 degradation. Remarkably, expression of the GAT domain significantly accelerated CXCR4 degradation following agonist treatment as compared to empty vector (FIGS. 6B and 6C). Taken together these data suggested that the STAM-1/arrestin-2 interaction negatively regulates CXCR4 sorting to lysosomes. As the STAM-1 GAT domain has been shown recently to bind to HRS and is predicted to be required for the assembly of ESCRT-0 (Ren et al., 2009), it is conceivable that arrestin-2 binding to STAM-1 displaces its interaction with HRS and promotes disassembly of ESCRT-0, which somehow negatively regulates the amount of CXCR4 that is targeted for lysosomal degradation.

To gain greater insight into this process, the investigation next set out to identify the STAM-1 binding region on arrestin-2 by truncation mutagenesis. Schematic representations of the arrestin-2 truncation mutants used are shown in FIG. 7A, generally as has been previously described (Bhandari et al., 2007). GST-STAM-1 and GST were incubated with lysates prepared from HEK293 cells expressing various HA-tagged arrestin-2 truncation mutants. The results from these binding experiments are summarized in FIG. 7A and the data are shown in FIG. 12. Both the N- and C-terminal regions of arrestin-2 bound to GST-STAM1, but not GST, although binding to the N-terminal region appeared to be stronger, suggesting that it represented the main binding region. Further deletion of this region revealed that the STAM-1 binding site on arrestin-2 is between amino acid residues 1-161 (FIG. 12B). The investigation next determined if expression of this region as a minigene in cells also disrupted the arrestin-2/STAM-1 interaction. However, when expressed in cells the arrestin-2-(1-161) minigene completely blocked CXCR4 degradation (data not shown). N-terminal lysine residues within arrestin-2 are predicted to serve as phosphosensors and recognize phosphates attached to receptors (Kern, R. C., Kang, D. S., and Benovic, J. L., Arrestin2/clathrin interactionis regulated by key- and C-terminal regions in arrestin2, Biochemistry 48, 7190-7200 (2009), analogous to what has been observed for arrestin-1 (Vishnivetskiy, S. A., Schubert, C., Climaco, G. C., Gurevich, Y. V., Velez, M. G., and Gurevich, V. V. An additional phosphate-binding element in arrestin molecule, Implications for the mechanism of arrestin activation, J. Biol. Chem. 275, 41049-41057 (2000). Therefore the arrestin-2-(1-161) construct may bind to CXCR4 and have a dominant negative effect on CXCR4 internalization. To rule out any effects at the level of internalization, the first twenty-four amino acids from the N-terminus of arrestin-2 were deleted to create arrestin-2-(25-161) and the investigation initially tested the ability of this mutant to bind to STAM-1. As shown in FIG. 7B, GST fused to arrestin-2-(25-161), but not GST alone, efficiently bound to FLAG-STAM-1 expressed in cells. A FLAG-tagged construct of arrestin-2-(25-161) when expressed in HEK293 cells also bound to GST-STAM-1-GAT, suggesting that the STAM-1/GAT domain binding site on arrestin-2 is located between amino acid residues 25-161 (FIG. 7C).

The investigation next examined whether expression of arrestin-2-(25-161) disrupted the STAM-1/arrestin-2 interaction and modulated CXCR4 degradation. Expression of FLAG-arrestin-2-(25-161) markedly disrupted the interaction between arrestin-2 and STAM-1 (FIG. 8A) and significantly accelerated agonist-promoted degradation of CXCR4

Figure 6:
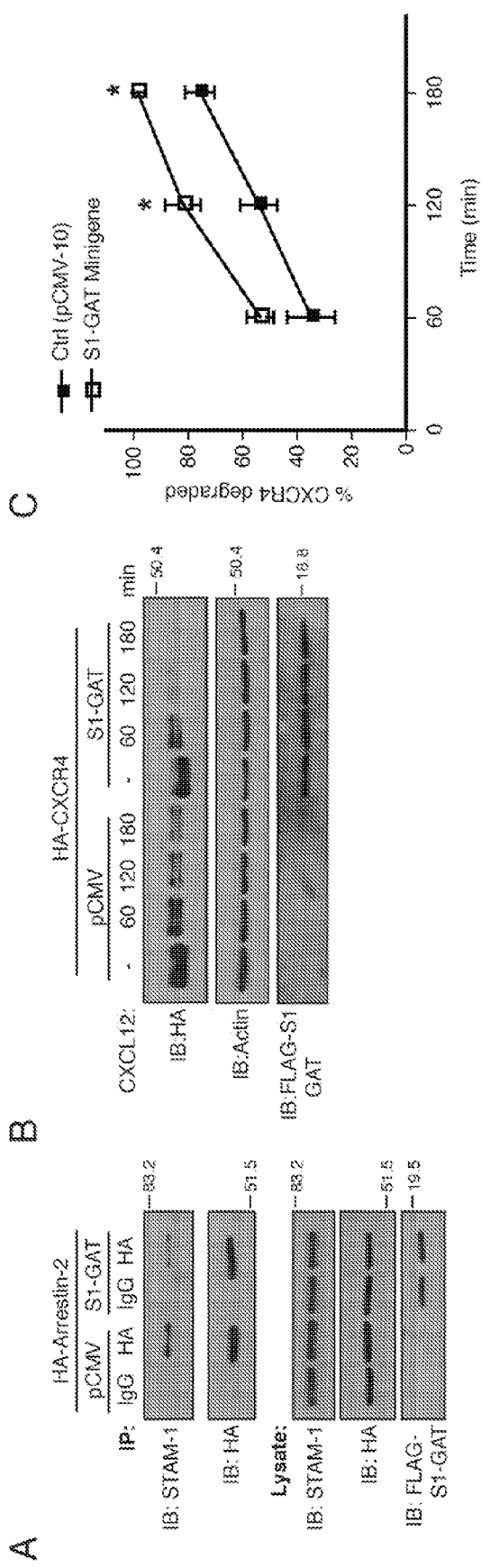
FIG. 6 illustrates that the expression of the GAT domain disrupts the arrestin-2/STAM-1 interaction and accelerates CXCR4 degradation.

(FIGS. 8B and 8C), similar to what was observed with the STAM-1 GAT domain (FIG. 6). Taken together these data further indicated that the interaction between STAM-1 and arrestin-2 attenuates CXCR4 trafficking into the degradative pathway.

Finally, the investigation turned to examining role of the arrestin-2/STAM-1 interaction on the ubiquitination status of CXCR4, STAM-1 and HRS. STAM, through its interaction with several deubiquitinating enzymes, may regulate the ubiquitination status of both cargo and of itself (McCullough et al., 2006; Row et al., 2006). Therefore, one possibility is that the STAM-1/arrestin-2 interaction modulates the ubiquitination status of CXCR4 and STAM-1, thereby facilitating CXCR4 trafficking into the degradative pathway. To examine this possibility, the investigation examined the effect of expressing the GAT domain on the ubiquitination status of both CXCR4 and STAM-1. Surprisingly, expression of the GAT, as compared to empty vector, did not significantly change the ubiquitination status of CXCR4 (FIG. 9A) and STAM-1 (FIG. 9B), suggesting that the STAM-1/arrestin-2 interaction does not regulate their ubiquitination status. In sharp contrast, expression of the GAT domain blocked CXCR4 mediated ubiquitination of HRS (FIG. 9C). Therefore, taken together, the data showed that the STAM-1/arrestin-2 interaction is critical for modulating ubiquitination of HRS, which is likely important for regulating sorting of CXCR4 into the degradative pathway.

Figure 10:
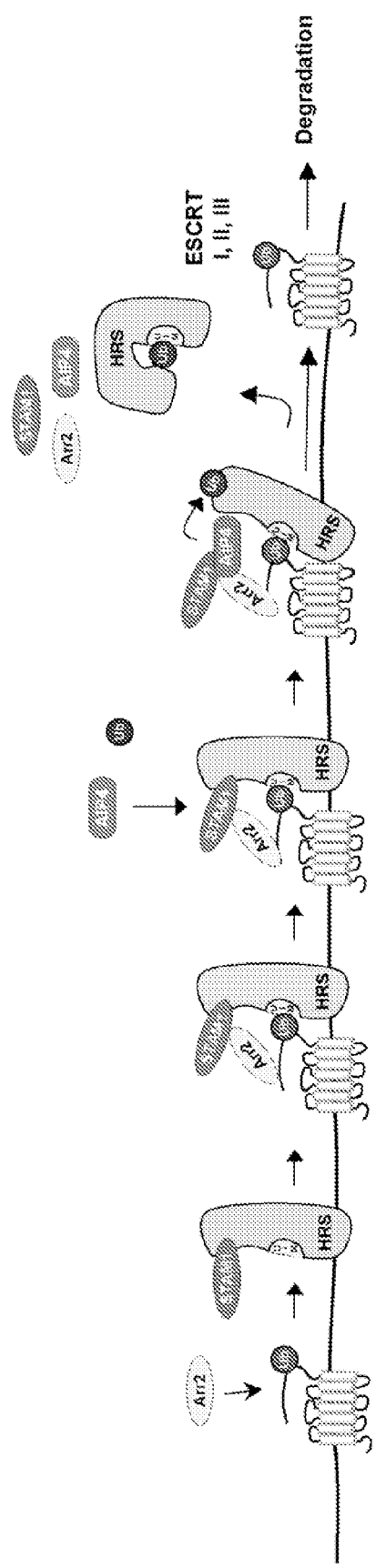
FIG. 10 schematically represents a proposed mechanism for the role of the STAM-1/arrestin-2 complex in endosomal sorting of CXCR4. CXCR4 is ubiquitinated by the E3 ubiquitin ligase AIP4 at the plasma membrane, after which it is internalized onto early endosomes, although ubiquitination is not required for this process. Endosomes ubiquitinated CXCR4 is recognized by HRS, likely by an interaction involving the ubiquitin moiety (red) on CXCR4 and the UIM of HRS, and possibly via an interaction with arrestin-2. Arrestin-2 then interacts with STAM-1, which serves to recruit AIP4 culminating in the ubiquitination of HRS. It is speculated that this may trigger a conformational change in HRS induced by an interaction between the ubiquitin moiety (blue) and the internal UIM. CXCR4 is subsequently committed to downstream interactions with ESCRT-I-III, while arrestin-2, STAM-1, AIP4 and auto-inhibited HRS are recycled such that another round of sorting can take place.

Non-visual arrestins are known for their ability to mediate GPCR desensitization, trafficking and signaling (Moore et al., 2007; Kovacs, J. J., Hara, M. R., Davenport, C. L., Kim, J., and Lefkowitz, R. J., Arrestin development: emerging roles for beta-arrestins ain developmental signaling pathways, Dev. Cell 17, 443-458 (2009). It has been reported that arrestin-2 interacts with AIP4 and mediates endosomal sorting of CXCR4 into the degradative pathway (Bhandari et al., 2007). The investigation reported above extended these findings to provide further mechanistic insight into this unprecedented role of arrestin-2. The data suggested that arrestin-2 mediates multiple interactions with ESCRT-0 on early endosomes, serving to regulate the amount of CXCR4 that is degraded. In view of the results of the investigation, it is believed that arrestin-2 likely links ubiquitinated CXCR4 to ESCRT-0 via an initial interaction with HRS and/or STAM-1. Interestingly, the data revealed that the arrestin-2 interaction with STAM-1 is important for regulating ubiquitination of HRS, which was believed to attenuate HRS sorting function, thereby controlling the extent to which CXCR4 is degraded. Such a mechanism is schematically depicted in FIG. 10.

Figure 3:
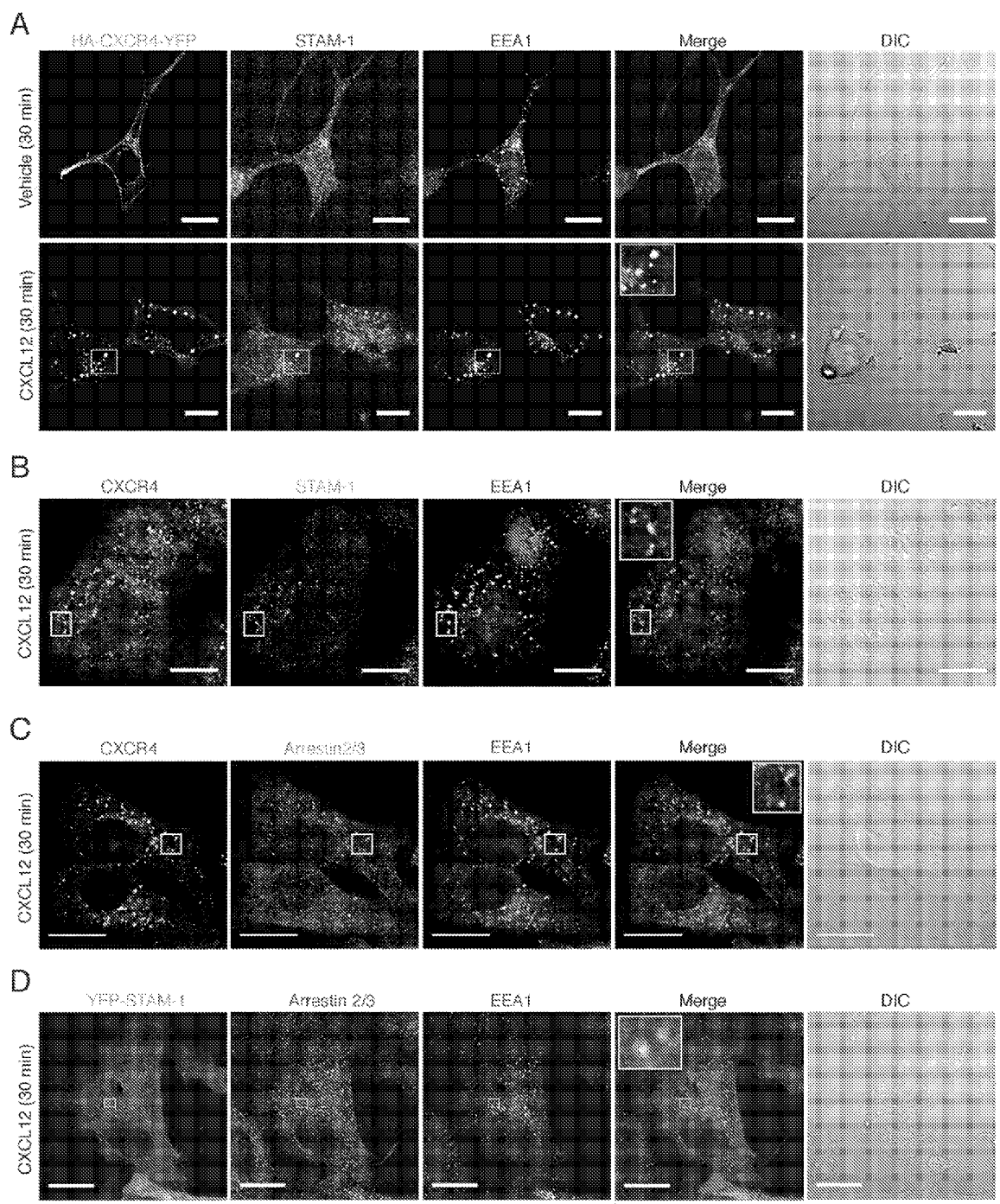
FIG. 3 contains representative micrographs from three independent experiments (bars=20 μm), and illustrates the co-localization of Arrestin-2, STAM-1 and CXCR4 on early endosomes.
Figure 13:
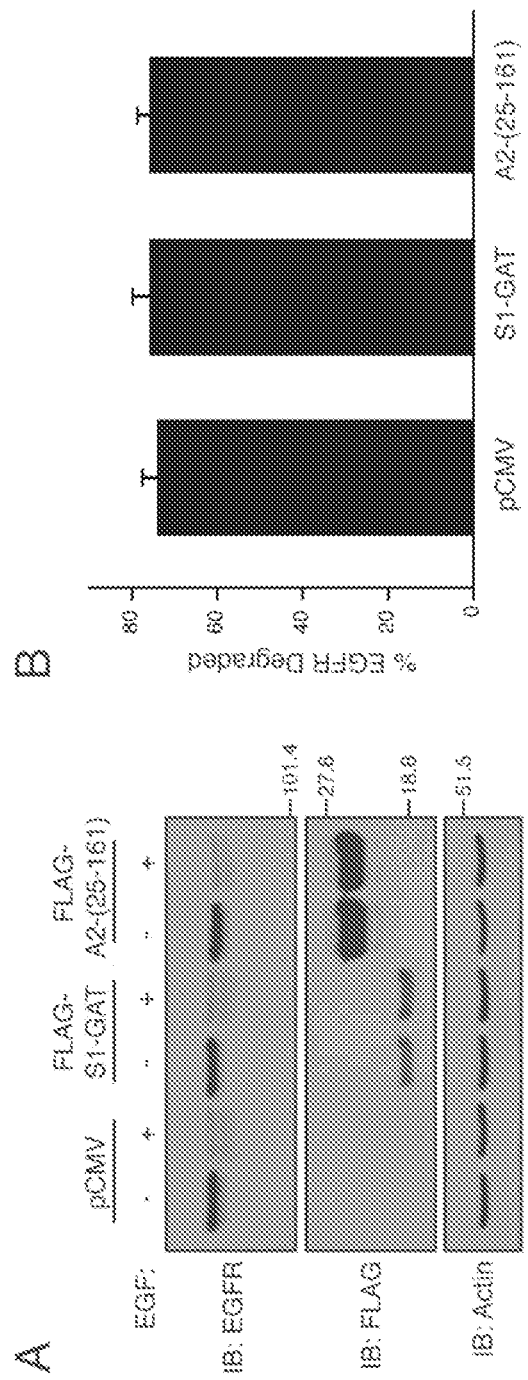
FIG. 13A represents data obtained when EGFR (epidermal growth factor receptor) degradation was assessed in HeLa cells transfected with FLAG-STAM-1-GAT, FLAG-Arr-2-(25-161) or pCMV. Cells were treated with about 100 ng/ml EFG for about one hour, followed by immunoblotting as described below. Shown are representative immunoblots from one of three independent experiments.
FIG. 13B is a bar graph that represents the amount of EGFR degraded as compared to vehicle treated cells±S.E.M. from three independent experiments. Data were analyzed by one-way analysis of variance and were found not to be significantly different.

The investigation employed truncation mutagenesis to narrow the arrestin-2 binding region on STAM-1 to the GAT domain and the STAM-1 binding region on arrestin-2 to amino acid residues 25-161. Expression of both of these domains similarly disrupted the arrestin-2/STAM-1 interaction and enhanced against promoted degradation of CXCR4. The data obtained in the investigation were consistent with the notion that the STAM-1/arrestin-2 interaction negatively regulates sorting of CXCR4 into the degradative pathway. This interaction may be specific to modulating CXCR4 and/or GPCR sorting, as EGFR degradation was not altered by expression of the STAM-1 GAT domain and arrestin-2-(25-161) (FIG. 13). Depletion of STAM-1 by siRNA also enhanced CXCR4 degradation, further revealing that STAM-1 negatively regulates CXCR4 endosomal sorting (FIG. 4A). In contrast, it had been previously shown that arrestin-2 promotes CXCR4 sorting (Bhandari et al., 2007) which, when considered with the data obtained in the investigation, indicates that arrestin-2 has opposing effects on CXCR4 degradation. This suggests that arrestin-2 likely acts at multiple steps in the sorting process and may initially act upstream of STAM-1 to positively regulate sorting of CXCR4 into the degradative pathway. Arrestin-2 interacts with the C-tail of CXCR4 (Busillo, J. M., Armando, S., Sengupta, R., Meucci, O., Bouvier, M., and Benovic, J. L., Site-specific phosphorylation of CXCR4 is dynamically regulated by multiple kinases and results in differential modulation of CXCR4 signaling, J. Biol. Chem., 285, 7805-7817 (2010), and therefore it is possible that arrestin-2 binds to CXCR4 on endosomes in order to recruit CXCR4 to ESCRT-0, possibly through an interaction with either HRS and/or STAM-1. This is consistent with the data from the investigation that showed that arrestin-2 co-localizes with CXCR4 and STAM-1 on early endosomes upon agonist activation (FIG. 3). Interestingly, a recent study found that Rim8, a *S. cerevisiae* molecule distantly related to mammalian arrestins, may function to directly recruit a putative 7™ receptor to the ESCRT machinery (Herrador, A., Herranz, S., Lara, D., and Vincent, O., Recruitment of the ESCRT machinery to a putative seven transmembrane-domain receptor is mediated by an arrestin-related protein, Mol. Cell Biol. 30, 897-907 (2010). After arrestin-2 initially directs CXCR4 to ESCRT-0, this is likely followed by an interaction with STAM-1 to attenuate CXCR4 degradation. Therefore, the results from the investigation are consistent with a model in which arrestin-2 influences CXCR4 sorting positively and negatively, and it is a balance of these two activities that dictates the extent to which CXCR4 is degraded.

The investigation led to the question as to how STAM-1 mediates the negative action of arrestin-2 on CXCR4 degradation. As ubiquitination of HRS is markedly reduced by expression of the GAT domain, it is likely that STAM-1 via its interaction with arrestin-2 regulates the ubiquitination status of HRS to control CXCR4 degradation. This suggests that CXCR4 promoted ubiquitination of HRS (FIG. 9C; Marchese et al. (2003)) attenuates its sorting activity. HRS contains a UIM that is thought to bind to ubiquitin moieties on cargo to recruit them into the degradative pathway (Hirano, S., Kawasaki, M., Ura, H., Kato, R., Raiborg, C., Stenmark, H., and Wakatsuki, S., Double-sided ubiquitin binding of Hrs-UIM in endosomal protein sorting, Nat. Struct. Mol. Biol. 13, 272-277 (2006). Interestingly, monoubiquitination of UBD containing proteins is thought to induce an intramolecular interaction between the ubiquitin moiety and the internal UBD, which in a protein such as HRS may induce an auto-inhibitory conformation such that it can no longer bind to ubiquitin moieties on cargo (Hoeller, D., Crosetto, N., Blagoev, B., Raiborg, C., Tikkanen, R., Wagner, S., Kowanetz, K., Breitling, R., Mann, M., Stenmark, H., Dikic, I., Regulation of ubiquitin-binding proteins by monoubiquitination, Nat. Cell Biol. 8, 163-169 (2006). As HRS ubiquitination is reduced by expression of the GAT domain, a loss of auto-inhibition likely enhances its sorting function culminating in enhanced degradation of CXCR4. Therefore, CXCR4 promoted ubiquitination of HRS may occur once HRS has completed its sorting function and CXCR4 has been committed to downstream elements of the degradative pathway (FIG. 10).

The investigation also raised the question as to how arrestin-2/STAM-1 regulates the ubiquitination status of HRS. It was previously shown that arrestin-2 interacts with AIP4 to regulate endosomal sorting of CXCR4 (Bhandari et al., 2007) and that AIP4 mediates agonist-promoted ubiquitination of HRS (Marchese et al., 2003). Therefore it is possible that arrestin-2, together with STAM-1, may serve to bridge AIP4 and HRS in order to facilitate HRS ubiquitination by AIP4.

Figure 8:
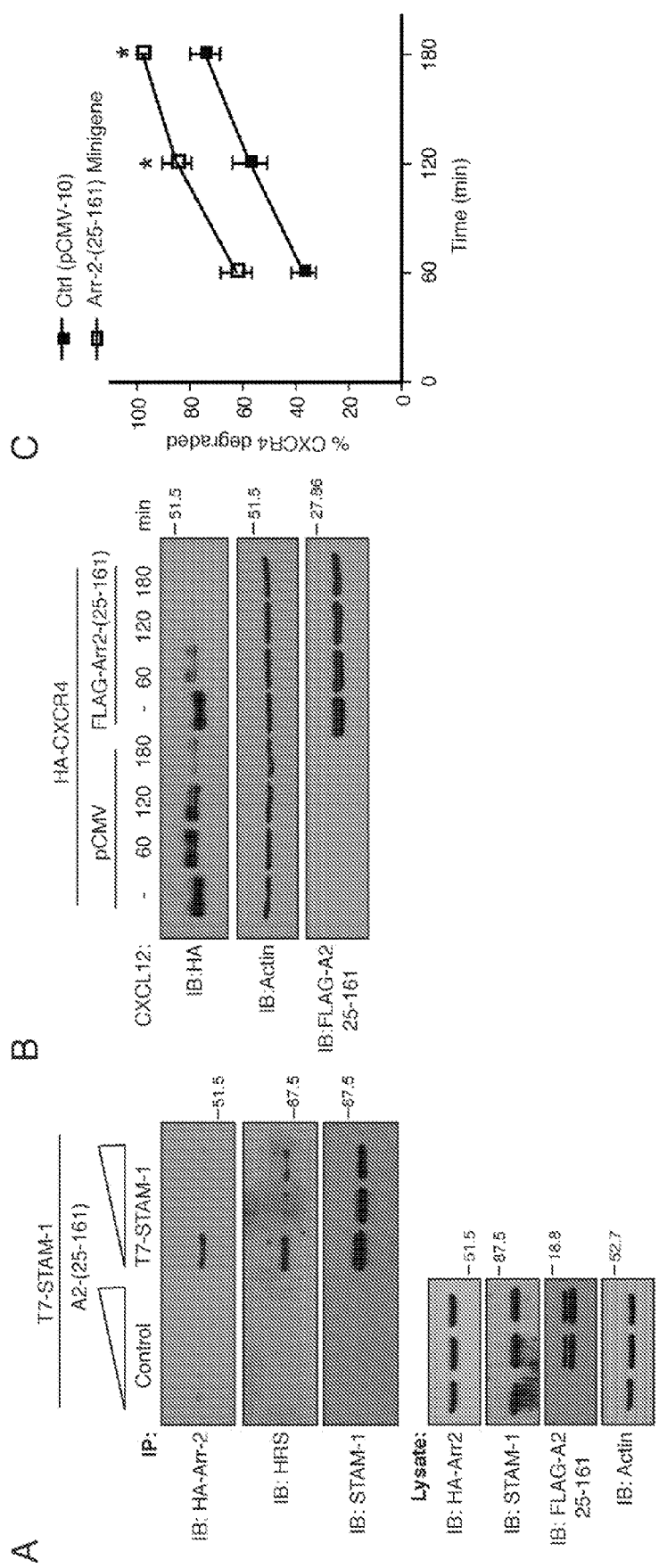
FIG. 8 illustrates that the expression of Arr2-(25-161) disrupts the STAM-1/arrestin-2 interaction and accelerates CXCR4 degradation.
Figure 9:
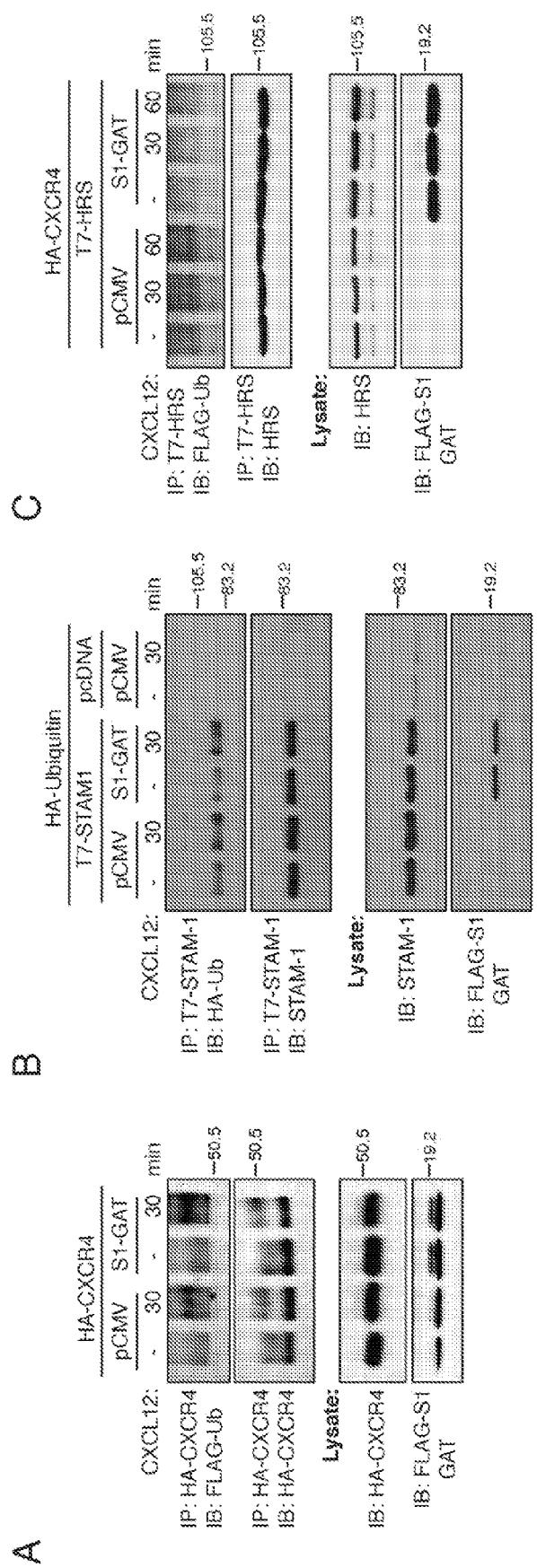
FIG. 9 illustrates that disrupting the STAM-1/arrestin-2 interaction inhibits HRS ubiquitination but does not effect on CXCR4 and STAM-1 ubiquitination.

This is consistent with the investigation's data that showed that expression of arrestin-2-(25-161) also displaces HRS binding to arrestin-2/STAM-1 (FIG. 8A). Alternatively, the arrestin-2/STAM-1 complex may regulate HRS deubiquitination. STAM has been shown to interact with deubiquitinating enzymes, such as AMSH and UBPY, which have been shown to regulate the ubiquitination status of cargo (for example, EGFR, protease activated receptor 2) and/or of STAM itself (McCullough et al., 2004; Row et al., 2006; Hasdemir, B., Murphy, J. E., Cottrell, G. S., and Bunnett, N. W., Endosomal deubiquitinating enzymes control ubiquitination and down-regulation of protease-activated receptor 2, J. Biol. Chem. 284, 28453-28466 (2009). However, from the investigation, the arrestin-2/STAM-1 complex does not appear to modulate the ubiquitination status of CXCR4 or STAM-1 (FIG. 9). In addition, depletion of AMSH did not affect agonist-promoted degradation of CXCR4 (FIG. 4D), suggesting that it may not be linked to this process, although it does not exclude the possibility that other DUBs may be involved (Row et al., 2006; Shenoy, S. K., Modi, A. S., Shukla, A. K., Xiao, K., Berthouze, M., Ahn, S., Wilkinson, K. D., Miller, W. E., and Lefkowitz, R. J., Beta-arrestin-dependent signaling and trafficking of 7-transmembrane receptors is reciprocally regulated by the deubiquitinase USP33 and the E3 ligase Mdm2. Proc. Nat. Acad. Sci. USA 106, 6650-6655 (2009). Nevertheless, the results of the investigation were consistent with the notion that the arrestin-2/STAM-1 complex mediates ubiquitination of HRS likely via AIP4.

Interestingly, the investigation appeared to indicate that STAM-2 is excluded from endosomal sorting of CXCR4, since arrestin-2 binds selectively to STAM-1 (FIG. 1A). This suggests that CXCR4 sorting is restricted to ESCRT-0 complexes that contain STAM-1 but not STAM-2. It was also observed through the investigation that activation of CXCR4 selectively enhances STAM-1 ubiquitination over STAM-2 (FIG. 2B), further supporting the selectivity of STAM-1 towards CXCR4. However, the arrestin-2/STAM-1 interaction may not be linked to STAM-1 ubiquitination (FIG. 9B). Presently, the function of STAM-1 ubiquitination on CXCR4 trafficking remains unknown, although it is possible that it may have a role in some other aspect of CXCR4 related functions. Though polyubiquitination of STAM has been linked to its degradation (Row et al., 2006), it is doubtful that CXCR4 regulates STAM-1 stability as no differences were observed in STAM-1 levels in cells treated with CXCL12 (data not shown).

Figure 15:
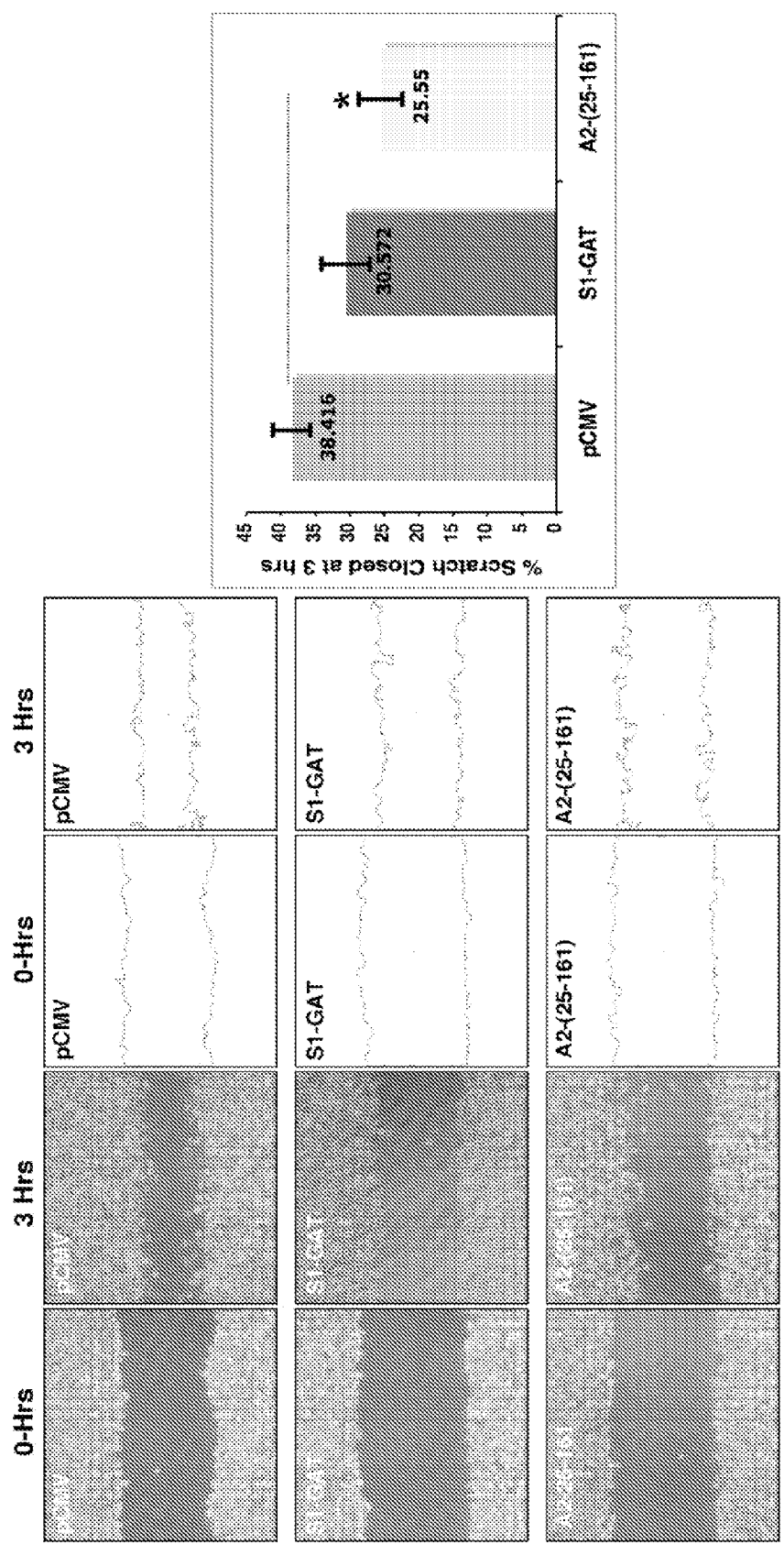
FIGS. 15 and 16 represent data obtained when cell migration was assessed by in vitro scratch assays and trans well assays, respectively.
Figure 16:
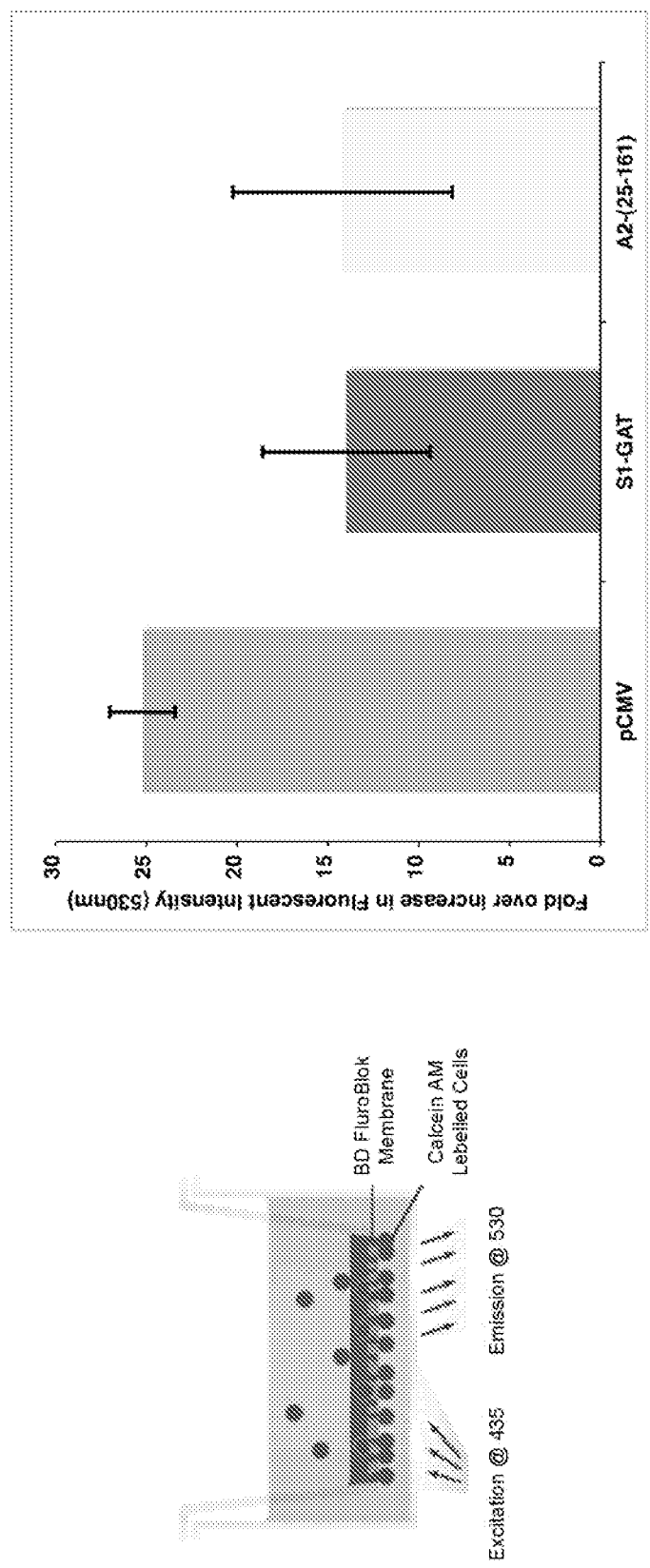

In another series of investigations, further work was conducted with the minigenes STAM-1(296-380) (referred to as STAM-1-GAT-domain above) and Arr2(25-161) whereby it was shown that when expressed in cells they attenuate cell migration induced by SDF-1α activation of CXCR4. Cell migration was monitored using two distinct commonly in vitro assays: a scratch assay (FIG. 15) and a trans well assay (FIG. 16). The results of both showed that STAM-1(296-380) and Arr2(25-161) expression in cells attenuates CXCR4-mediated cell migration. The data obtained with this investigation provided significant mechanistic insight into the molecular pathways that mediate CXCR4-induced cell migration and establish the STAM-1/arrestin-2 complex as a potential therapeutic target to treat cancer metastasis.

On the basis of the above, it can be appreciated that the investigation provided a mechanistic insight into the role of arrestin-2 in endosomal sorting of CXCR4 via multiple interactions with ESCRT-0. The investigation revealed that, via an interaction with STAM-1, arrestin-2 serves as an adaptor to regulate endosomal ubiquitination events that are critical for regulating the sorting of ubiquitinated CXCR4 into the degradative pathway, thereby controlling the amount of CXCR4 that is degraded. On this basis, it was concluded that an interaction between the adaptor proteins arrestin-2 and STAM-1 enables the arrestin-2/STAM-1 complex to be used as a therapeutic target to modulate CXCR4 levels and to modulate CXCL12-evoked cell migration. This aspect of the invention can be extended to the use of the arrestin-2/STAM-1 complex to identify and develop novel pharmacological agents capable of targeting the arrestin-2/STAM-1 interaction for therapeutic intervention, for example, to treat metastasis in cancer patients, and in particular patients with cancers that exhibit elevated levels of CXCR4 in the tumor cells.

Though the invention has been described in terms of observations and results obtained during an investigation in which a particular series of procedures was performed, the scope of the invention is to be limited only by the following claims.

The invention claimed is:

1. A method of screening for therapeutic agents that modulate endosomal sorting of the CXC chemokine receptor 4 (CXCR4) in a target cell, the method comprising treating the target cell with a candidate therapeutic agent which mediates or attenuates an interaction between an arrestin-2 adapter protein molecule and a STAM-1 adapter protein molecule, where the interaction is characterized by the arrestin-2 adapter protein molecule directly binding to the STAM-1 adapter protein molecule.

2. The method according to claim 1, wherein the interaction between the arrestin-2 adapter protein molecule and the STAM-1 adapter protein molecule is mediated to modulate CXCR4 levels and signaling in the target cell.

3. The method according to claim 1, wherein the interaction between the arrestin-2 adapter protein molecule and the STAM-1 adapter protein molecule is mediated to modulate CXCL12-evoked cell migration in the target cell.

4. The method according to claim 1, wherein the interaction between the arrestin-2 adapter protein molecule and the STAM-1 adapter protein molecule is enhanced by the treating step.

5. The method according to claim 4, wherein the enhancement of the interaction between the arrestin-2 adapter protein molecule and the STAM-1 adapter protein molecule promotes CXCL12-evoked cell migration in the target cell.

6. The method according to claim 1, wherein the interaction between the arrestin-2 adapter protein molecule and the STAM-1 adapter protein molecule is disrupted by the treating step.

7. The method according to claim 1, wherein the treating step comprises subjecting a target cell to a pharmacological agent, and determining whether the pharmacological agent disrupts or enhances the interaction between the arrestin-2 adapter protein molecule and the STAM-1 adapter protein molecule.

8. The method of claim 7, wherein the method further comprises identifying therapeutic candidates for treating a myocardial infarction or stroke in a patient.

9. The method according to claim 7, wherein the interaction between the arrestin-2 adapter protein molecule and the STAM-1 adapter protein molecule is enhanced by the treating step.

10. The method according to claim 9, wherein the enhancement of the interaction between the arrestin-2 adapter protein molecule and the STAM-1 adapter protein molecule in the target cell.

11. The method according to claim 9, wherein the enhancement of the interaction between the arrestin-2 adapter protein molecule and the STAM-1 adapter protein molecule reduces; CXCR4 levels in the target cell.

12. The method according to claim 7, wherein the interaction between the arrestin-2 adapter protein molecule and the STAM-1 adapter protein molecule is disrupted by the treating step.

13. The method according to claim 12, wherein the disruption of the interaction between the arrestin-2 adapter protein molecule and the STAM-1 adapter protein molecule accelerates degradation of CXCR4 in the target cell.

14. The method according to claim 12, wherein the disruption of the interaction between the arrestin-2 adapter protein molecule and the STAM-1 adapter protein molecule decreases CXCR4 levels in the target cell.

15. The method according to claim 12, wherein the disruption of the interaction between the arrestin-2 adapter protein molecule and the STAM-1 adapter protein molecule inhibits CXCL12-evoked cell migration in the target cell.

16. The method according to claim 12, wherein the disruption of the interaction between the arrestin-2 adapter protein molecule and the STAM-1 adapter protein molecule promotes CXCL12-evoked cell migration of the target cell.

17. The method of claim 8, wherein the method further comprises identifying therapeutic candidates for treating metastasis of a cancer in a patient.

18. The method according to claim 17, wherein the cancer is characterized by an elevated level of CXCR4 in tumor cells.

19. The method of claim 17, wherein the therapeutic candidate inhibits migration of tumor cells.

* * * * *

SEQUENCE LISTING

<160> NUMBER OF SEQ ID NOS: 6

<210> SEQ ID NO 1
<211> LENGTH: 418
<212> TYPE: PRT
<213> ORGANISM: Homo sapiens

<400> SEQUENCE: 1

Met Gly Asp Lys Gly Thr Arg Val Phe Lys Lys Ala Ser Pro Asn Gly
1               5                   10                  15

Lys Leu Thr Val Tyr Leu Gly Lys Arg Asp Phe Val Asp His Ile Asp
            20                  25                  30

Leu Val Glu Pro Val Asp Gly Val Val Leu Val Asp Pro Glu Tyr Leu
        35                  40                  45

Lys Glu Arg Arg Val Tyr Val Thr Leu Thr Cys Ala Phe Arg Tyr Gly
    50                  55                  60

Arg Glu Asp Leu Asp Val Leu Gly Leu Thr Phe Arg Lys Asp Leu Phe
65                  70                  75                  80

Val Ala Asn Val Gln Ser Phe Pro Pro Ala Pro Glu Asp Lys Lys Pro
            85                  90                  95

Leu Thr Arg Leu Gln Glu Arg Leu Ile Lys Lys Leu Gly Glu His Ala
            100                 105                 110

Tyr Pro Phe Thr Phe Glu Ile Pro Pro Asn Leu Pro Cys Ser Val Thr
            115                 120                 125

Leu Gln Pro Gly Pro Glu Asp Thr Gly Lys Ala Cys Gly Val Asp Tyr
        130                 135                 140

Glu Val Lys Ala Phe Cys Ala Glu Asn Leu Glu Lys Ile His Lys
145                 150                 155                 160

Arg Asn Ser Val Arg Leu Val Ile Arg Lys Val Gln Tyr Ala Pro Glu
            165                 170                 175

Arg Pro Gly Pro Gln Pro Thr Ala Glu Thr Thr Arg Gln Phe Leu Met
            180                 185                 190

Ser Asp Lys Pro Leu His Leu Glu Ala Ser Leu Asp Lys Glu Ile Tyr
            195                 200                 205

Tyr His Gly Glu Pro Ile Ser Val Asn Val His Val Thr Asn Asn Thr
        210                 215                 220

Asn Lys Thr Val Lys Lys Ile Lys Ile Ser Val Arg Gln Tyr Ala Asp
225                 230                 235                 240

Ile Cys Leu Phe Asn Thr Ala Gln Tyr Lys Cys Pro Val Ala Met Glu
            245                 250                 255

Glu Ala Asp Asp Thr Val Ala Pro Ser Ser Thr Phe Cys Lys Val Tyr
            260                 265                 270

Thr Leu Thr Pro Phe Leu Ala Asn Asn Arg Glu Lys Arg Gly Leu Ala
        275                 280                 285

Leu Asp Gly Lys Leu Lys His Glu Asp Thr Asn Leu Ala Ser Ser Thr
            290                 295                 300

Leu Leu Arg Glu Gly Ala Asn Arg Glu Ile Leu Gly Ile Ile Val Ser
305                 310                 315                 320

Tyr Lys Val Lys Val Lys Leu Val Val Ser Arg Gly Gly Leu Leu Gly
            325                 330                 335

Asp Leu Ala Ser Ser Asp Val Ala Val Glu Leu Pro Phe Thr Leu Met
            340                 345                 350

His Pro Lys Pro Lys Glu Glu Pro Pro His Arg Glu Val Pro Glu His
            355                 360                 365

Glu Thr Pro Val Asp Thr Asn Leu Ile Glu Leu Asp Thr Asn Asp Asp
        370                 375                 380

Asp Ile Val Phe Glu Asp Phe Ala Arg Gln Arg Leu Lys Gly Met Lys
385                 390                 395                 400

Asp Asp Lys Glu Glu Glu Asp Gly Thr Gly Ser Pro Arg Leu Asn
            405                 410                 415

Asp Arg

<210> SEQ ID NO 2
<211> LENGTH: 410
<212> TYPE: PRT
<213> ORGANISM: Homo sapiens

<400> SEQUENCE: 2

Met Gly Glu Lys Pro Gly Thr Arg Val Phe Lys Lys Ser Ser Pro Asn
1               5                   10                  15

Cys Lys Leu Thr Val Tyr Leu Gly Lys Arg Asp Phe Val Asp His Leu
            20                  25                  30

```
Asp Lys Val Asp Pro Val Asp Gly Val Val Leu Val Asp Pro Asp Tyr
         35                  40                  45
Leu Lys Asp Arg Lys Val Phe Val Thr Leu Thr Cys Ala Phe Arg Tyr
 50                  55                  60
Gly Arg Glu Asp Leu Asp Val Leu Gly Leu Ser Phe Arg Lys Asp Leu
 65                  70                  75                  80
Phe Ile Ala Asn Tyr Gln Ala Phe Pro Pro Thr Pro Asn Pro Pro Arg
                 85                  90                  95
Pro Pro Thr Arg Leu Gln Glu Arg Leu Leu Arg Lys Leu Gly Gln His
            100                 105                 110
Ala His Pro Phe Phe Thr Ile Pro Gln Asn Leu Pro Cys Ser Val
        115                 120                 125
Thr Leu Gln Pro Gly Pro Glu Asp Thr Gly Lys Ala Cys Gly Val Asp
130                 135                 140
Phe Glu Ile Arg Ala Phe Cys Ala Lys Ser Leu Glu Lys Ser His
145                 150                 155                 160
Lys Arg Asn Ser Val Arg Leu Val Ile Arg Lys Val Gln Phe Ala Pro
                165                 170                 175
Glu Lys Pro Gly Pro Gln Pro Ser Ala Glu Thr Thr Arg His Phe Leu
            180                 185                 190
Met Ser Asp Arg Ser Leu His Leu Glu Ala Ser Leu Asp Lys Glu Leu
        195                 200                 205
Tyr Tyr His Gly Glu Pro Leu Asn Val Asn Val His Val Thr Asn Asn
210                 215                 220
Ser Thr Lys Thr Val Lys Lys Ile Lys Val Ser Val Arg Gln Tyr Ala
225                 230                 235                 240
Asp Ile Cys Leu Phe Ser Thr Ala Gln Tyr Lys Cys Pro Val Ala Gln
                245                 250                 255
Val Glu Gln Asp Asp Gln Val Ser Pro Ser Ser Thr Phe Cys Lys Val
            260                 265                 270
Tyr Thr Ile Thr Pro Leu Leu Ser Asn Asn Arg Glu Lys Arg Gly Leu
        275                 280                 285
Ala Leu Asp Gly Lys Leu Lys His Glu Asp Thr Asn Ala Asn Lys Glu
290                 295                 300
Val Leu Gly Ile Leu Val Ser Tyr Arg Val Lys Val Lys Leu Val Val
305                 310                 315                 320
Ser Arg Gly Gly Asp Val Ser Val Glu Leu Pro Phe Val Leu Met His
                325                 330                 335
Pro Lys Pro His Asp His Ile Ala Leu Pro Arg Pro Gln Ser Ala Pro
            340                 345                 350
Thr His Pro Pro Thr Leu Leu Pro Ser Ala Val Pro Glu Thr Asp Ala
        355                 360                 365
Pro Val Asp Thr Asn Leu Ile Glu Phe Glu Thr Asn Tyr Ala Thr Asp
370                 375                 380
Asp Asp Ile Val Phe Glu Asp Phe Ala Arg Leu Arg Leu Lys Gly Leu
385                 390                 395                 400
Lys Asp Glu Asp Tyr Asp Asp Gln Phe Cys
                405                 410

<210> SEQ ID NO 3
<211> LENGTH: 136
<212> TYPE: PRT
<213> ORGANISM: Homo sapiens

<400> SEQUENCE: 3
```

-continued

Arg Asp Phe Val Asp His Ile Asp Leu Val Glu Pro Val Asp Gly Val
1               5                   10                  15

Val Leu Val Asp Pro Glu Tyr Leu Lys Glu Arg Arg Val Tyr Val Thr
            20                  25                  30

Leu Thr Cys Ala Phe Arg Tyr Gly Arg Glu Asp Leu Val Leu Gly Leu
            35                  40                  45

Thr Phe Arg Lys Asp Leu Phe Val Ala Asn Val Gln Ser Phe Pro Pro
        50                  55                  60

Ala Pro Glu Asp Lys Lys Pro Leu Thr Arg Leu Gln Glu Arg Leu Ile
65                  70                  75                  80

Lys Lys Leu Gly Glu His Ala Tyr Pro Phe Thr Phe Glu Ile Pro Pro
                85                  90                  95

Asn Leu Pro Cys Ser Val Thr Leu Gln Pro Gly Pro Glu Asp Thr Gly
            100                 105                 110

Lys Ala Cys Gly Val Asp Tyr Glu Val Lys Ala Phe Cys Ala Glu Asn
        115                 120                 125

Leu Glu Glu Lys Ile His Lys Arg
        130                 135

<210> SEQ ID NO 4
<211> LENGTH: 540
<212> TYPE: PRT
<213> ORGANISM: Homo sapiens

<400> SEQUENCE: 4

Met Pro Leu Phe Ala Thr Asn Pro Phe Asp Gln Asp Val Glu Lys Ala
1               5                   10                  15

Thr Ser Glu Met Asn Thr Ala Glu Asp Trp Gly Leu Ile Leu Asp Ile
            20                  25                  30

Cys Asp Lys Val Gly Gln Ser Arg Thr Gly Pro Lys Asp Cys Leu Arg
            35                  40                  45

Ser Ile Met Arg Arg Val Asn His Lys Asp Pro His Val Ala Met Gln
        50                  55                  60

Ala Leu Thr Leu Leu Gly Ala Cys Val Ser Asn Cys Gly Lys Ile Phe
65                  70                  75                  80

His Leu Glu Val Cys Ser Arg Asp Phe Ala Ser Glu Val Ser Asn Val
                85                  90                  95

Leu Asn Lys Gly His Pro Lys Val Cys Glu Lys Leu Lys Ala Leu Met
            100                 105                 110

Val Glu Trp Thr Asp Glu Phe Lys Asn Asp Pro Gln Leu Ser Leu Ile
        115                 120                 125

Ser Ala Met Ile Lys Asn Leu Lys Glu Gln Gly Val Thr Phe Pro Ala
        130                 135                 140

Ile Gly Ser Gln Ala Ala Glu Gln Ala Lys Ala Ser Pro Ala Leu Val
145                 150                 155                 160

Ala Lys Asp Pro Gly Thr Val Ala Asn Lys Lys Glu Glu Glu Asp Leu
                165                 170                 175

Ala Lys Ala Ile Glu Leu Ser Leu Lys Glu Gln Arg Gln Gln Ser Thr
            180                 185                 190

Thr Leu Ser Thr Leu Tyr Pro Ser Thr Ser Ser Leu Leu Thr Asn His
        195                 200                 205

Gln His Glu Gly Arg Lys Val Arg Ala Ile Tyr Asp Phe Glu Ala Ala
        210                 215                 220

Glu Asp Asn Glu Leu Thr Phe Lys Ala Gly Glu Ile Ile Thr Val Leu
225                 230                 235                 240

-continued

```
Asp Asp Ser Asp Pro Asn Trp Trp Lys Gly Glu Thr His Gln Gly Ile
            245                 250                 255
Gly Leu Phe Pro Ser Asn Phe Val Thr Ala Asp Leu Thr Ala Glu Pro
            260                 265                 270
Glu Met Ile Lys Thr Glu Lys Lys Thr Val Gln Phe Ser Asp Asp Val
            275                 280                 285
Gln Val Glu Thr Ile Glu Pro Glu Pro Glu Pro Ala Phe Ile Asp Glu
290                 295                 300
Asp Lys Met Asp Gln Leu Leu Gln Met Leu Gln Ser Thr Asp Pro Ser
305                 310                 315                 320
Asp Asp Gln Pro Asp Leu Pro Glu Leu Leu His Leu Glu Ala Met Cys
                325                 330                 335
His Gln Met Gly Pro Leu Ile Asp Glu Lys Leu Glu Asp Ile Asp Arg
                340                 345                 350
Lys His Ser Glu Leu Ser Glu Leu Asn Val Lys Val Met Glu Ala Leu
                355                 360                 365
Ser Leu Tyr Thr Lys Leu Met Asn Glu Asp Pro Met Tyr Ser Met Tyr
            370                 375                 380
Ala Lys Leu Gln Asn Gln Pro Tyr Tyr Met Gln Ser Ser Gly Val Ser
385                 390                 395                 400
Gly Ser Gln Val Tyr Ala Gly Pro Pro Ser Gly Ala Tyr Leu Val
                405                 410                 415
Ala Gly Asn Ala Gln Met Ser His Leu Gln Ser Tyr Ser Leu Pro Pro
                420                 425                 430
Glu Gln Leu Ser Ser Leu Ser Gln Ala Val Val Pro Pro Ser Ala Asn
            435                 440                 445
Pro Ala Leu Pro Ser Gln Gln Thr Gln Ala Ala Tyr Pro Asn Thr Met
450                 455                 460
Val Ser Ser Val Gln Gly Asn Thr Tyr Pro Ser Gln Ala Pro Val Tyr
465                 470                 475                 480
Ser Pro Pro Pro Ala Ala Thr Ala Ala Ala Thr Ala Asp Val Thr
                485                 490                 495
Leu Tyr Gln Asn Ala Gly Pro Asn Met Pro Gln Val Pro Asn Tyr Asn
            500                 505                 510
Leu Thr Ser Ser Thr Leu Pro Gln Pro Gly Gly Ser Gln Gln Pro Pro
            515                 520                 525
Gln Pro Gln Gln Pro Tyr Ser Gln Lys Ala Leu Leu
            530                 535                 540

<210> SEQ ID NO 5
<211> LENGTH: 525
<212> TYPE: PRT
<213> ORGANISM: Homo sapiens

<400> SEQUENCE: 5

Met Pro Leu Phe Thr Ala Asn Pro Phe Glu Gln Asp Val Glu Lys Ala
1               5                   10                  15
Thr Asn Glu Tyr Asn Thr Thr Glu Asp Trp Ser Leu Ile Met Asp Ile
            20                  25                  30
Cys Asp Lys Val Gly Ser Thr Pro Asn Gly Ala Lys Asp Cys Leu Lys
        35                  40                  45
Ala Ile Met Lys Arg Val Asn His Lys Val Pro His Val Ala Leu Gln
    50                  55                  60
Ala Leu Thr Leu Leu Gly Ala Cys Val Ala Asn Cys Gly Lys Ile Phe
65                  70                  75                  80
```

```
His Leu Glu Val Cys Ser Arg Asp Phe Ala Thr Glu Val Arg Ala Val
                85                  90                  95

Ile Lys Asn Lys Ala His Pro Lys Val Cys Glu Lys Leu Lys Ser Leu
            100                 105                 110

Met Val Glu Trp Ser Glu Glu Phe Gln Lys Asp Pro Gln Phe Ser Leu
            115                 120                 125

Ile Ser Ala Thr Ile Lys Ser Met Lys Glu Glu Gly Ile Thr Phe Pro
130                 135                 140

Pro Ala Gly Ser Gln Thr Val Ser Ala Ala Lys Asn Gly Thr Ser
145                 150                 155                 160

Ser Asn Lys Asn Lys Glu Asp Glu Ile Ala Lys Ala Ile Glu Leu
                165                 170                 175

Ser Leu Gln Glu Gln Lys Gln Gln His Thr Glu Thr Lys Ser Leu Tyr
            180                 185                 190

Pro Ser Ser Glu Ile Gln Leu Asn Asn Lys Val Ala Arg Lys Val Arg
            195                 200                 205

Ala Leu Tyr Asp Phe Glu Ala Val Glu Asp Asn Glu Leu Thr Phe Lys
            210                 215                 220

His Gly Glu Ile Ile Val Leu Asp Asp Ser Asp Ala Asn Trp Trp
225                 230                 235                 240

Lys Gly Glu Asn His Arg Gly Ile Gly Leu Phe Pro Ser Asn Phe Val
                245                 250                 255

Thr Thr Asn Leu Asn Ile Glu Thr Glu Ala Ala Ala Val Asp Lys Leu
            260                 265                 270

Asn Val Ile Asp Asp Val Glu Ile Lys Lys Ser Glu Pro Glu
            275                 280                 285

Pro Val Tyr Ile Asp Glu Asp Lys Met Asp Arg Ala Leu Gln Val Leu
            290                 295                 300

Gln Ser Ile Asp Pro Thr Asp Ser Lys Pro Asp Ser Gln Asp Leu Leu
305                 310                 315                 320

Asp Leu Glu Asp Ile Cys Gln Gln Met Gly Pro Met Ile Asp Glu Lys
                325                 330                 335

Leu Glu Glu Ile Asp Arg Lys His Ser Glu Leu Ser Glu Leu Asn Val
            340                 345                 350

Lys Val Leu Glu Ala Leu Glu Leu Tyr Asn Lys Leu Val Asn Glu Ala
            355                 360                 365

Pro Val Tyr Ser Val Tyr Ser Lys Leu His Pro Ala His Tyr Pro
            370                 375                 380

Pro Ala Ser Ser Gly Val Pro Met Gln Thr Tyr Pro Val Gln Ser His
385                 390                 395                 400

Gly Gly Asn Tyr Met Gly Gln Ser Ile His Gln Val Thr Val Ala Gln
                405                 410                 415

Ser Tyr Ser Leu Gly Pro Asp Gln Ile Gly Pro Leu Arg Ser Leu Pro
            420                 425                 430

Pro Asn Val Asn Ser Val Thr Ala Gln Pro Ala Gln Thr Ser Tyr
            435                 440                 445

Leu Ser Thr Gly Gln Asp Thr Val Ser Asn Pro Thr Tyr Met Asn Gln
450                 455                 460

Asn Ser Asn Leu Gln Ser Ala Thr Gly Thr Thr Ala Tyr Thr Gln Gln
465                 470                 475                 480

Met Gly Met Ser Val Asp Met Ser Ser Tyr Gln Asn Thr Thr Ser Asn
                485                 490                 495

Leu Pro Gln Leu Ala Gly Phe Pro Val Thr Val Pro Ala His Pro Val
            500                 505                 510
```

```
Ala Gln Gln His Thr Asn Tyr His Gln Gln Pro Leu Leu
        515                 520                 525

<210> SEQ ID NO 6
<211> LENGTH: 161
<212> TYPE: PRT
<213> ORGANISM: Homo sapiens

<400> SEQUENCE: 6

Met Asp Tyr Lys Asp His Asp Gly Asp Tyr Lys Asp His Asp Ile Asp
1               5                   10                  15

Tyr Lys Asp Asp Asp Asp Lys Leu Arg Asp Phe Val Asp His Ile Asp
            20                  25                  30

Leu Val Glu Pro Val Asp Gly Val Val Leu Val Asp Pro Glu Tyr Leu
        35                  40                  45

Lys Glu Arg Arg Val Tyr Val Thr Leu Thr Cys Ala Phe Arg Tyr Gly
    50                  55                  60

Arg Glu Asp Leu Asp Val Leu Gly Leu Thr Phe Arg Lys Asp Leu Phe
65                  70                  75                  80

Val Ala Asn Val Gln Ser Phe Pro Pro Ala Pro Glu Asp Lys Lys Pro
                85                  90                  95

Leu Thr Arg Leu Gln Glu Arg Leu Ile Lys Lys Leu Gly Glu His Ala
            100                 105                 110

Tyr Pro Phe Thr Phe Glu Ile Pro Pro Asn Leu Pro Cys Ser Val Thr
        115                 120                 125

Leu Gln Pro Gly Pro Glu Asp Thr Gly Lys Ala Cys Gly Val Asp Tyr
    130                 135                 140

Glu Val Lys Ala Phe Cys Ala Glu Asn Leu Glu Glu Lys Ile His Lys
145                 150                 155                 160

Arg
```